United States Patent
Elia et al.

(10) Patent No.: US 11,278,473 B2
(45) Date of Patent: *Mar. 22, 2022

(54) MEDICAL PUMP

(71) Applicant: ART MEDICAL Ltd., Netanya (IL)

(72) Inventors: Liron Elia, Kiryat-Ata (IL); Gavriel J. Iddan, Haifa (IL); Evgeni Venislavski, Rosh HaAyin (IL); Nir Lilach, Kfar Yehoshua (IL)

(73) Assignee: ART MEDICAL Ltd., Netanya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/227,399

(22) Filed: Apr. 12, 2021

(65) Prior Publication Data

US 2021/0298995 A1 Sep. 30, 2021

Related U.S. Application Data

(63) Continuation of application No. 16/110,016, filed on Aug. 23, 2018, now Pat. No. 10,973,739.

(51) Int. Cl.
*A61J 15/00* (2006.01)
*A61M 5/145* (2006.01)
(Continued)

(52) U.S. Cl.
CPC ....... *A61J 15/0076* (2015.05); *A61J 15/0092* (2013.01); *A61M 5/1407* (2013.01);
(Continued)

(58) Field of Classification Search
CPC .... A61J 5/0076; A61J 5/0092; A61M 5/1407; A61M 5/1408; A61M 5/1413;
(Continued)

(56) References Cited

U.S. PATENT DOCUMENTS

| 3,874,407 | A | 4/1975 | Griswold |
| 7,384,410 | B2 | 6/2008 | Eggers et al. |

(Continued)

FOREIGN PATENT DOCUMENTS

| CA | 2640822 | 8/2006 |
| WO | WO 2018/096534 | 5/2018 |
| WO | WO 2020/039448 | 2/2020 |

OTHER PUBLICATIONS

Advisory Action Before the Filing of an Appeal Brief dated Feb. 12, 2020 From the US Patent and Trademark Office Re. U.S. Appl. No. 16/110,016. (4 pages).

(Continued)

*Primary Examiner* — Shefali D Patel

(57) ABSTRACT

A medical pump, comprising: a fluid housing having a plurality of intake openings, sealed by at least one intake valve, and an outlet opening sealed by an outlet valve; a piston which is sealing the fluid housing and connected to a drive mechanism, the drive mechanism pulls the piston to draw fluid from one of the plurality of intake openings and pushes the piston to discharge the fluid into the outlet opening; and a selecting valve enclosing at least two tubes, each providing fluid to one of the plurality of intake openings, wherein the selecting valve closes one of the at least two tubes while opening another of the at least two tubes.

17 Claims, 27 Drawing Sheets

(51) Int. Cl.
   *A61M 5/168*   (2006.01)
   *A61M 39/28*   (2006.01)
   *A61M 5/142*   (2006.01)
   *A61M 5/14*    (2006.01)

(52) U.S. Cl.
   CPC ........ *A61M 5/1413* (2013.01); *A61M 5/1452* (2013.01); *A61M 5/1456* (2013.01); *A61M 5/14216* (2013.01); *A61M 5/16813* (2013.01); *A61M 5/16827* (2013.01); *A61M 39/28* (2013.01); *A61J 15/0084* (2015.05); *A61M 5/1408* (2013.01); *A61M 2005/14573* (2013.01); *A61M 2205/18* (2013.01); *A61M 2205/50* (2013.01); *A61M 2205/502* (2013.01); *A61M 2205/6054* (2013.01)

(58) Field of Classification Search
   CPC .............. A61M 5/142; A61M 5/14212; A61M 5/14216; A61M 5/145; A61M 5/1452; A61M 5/1456; A61M 5/16809; A61M 5/16813; A61M 5/16827; A61M 5/16881; A61M 5/172; A61M 2005/14208; A61M 2005/14506; A61M 2005/14573; A61M 39/28; A61M 2205/12; A61M 2205/121; A61M 2205/123; A61M 2205/128; A61M 2205/50; A61M 2205/502; A61M 2039/0027
   See application file for complete search history.

(56) References Cited

U.S. PATENT DOCUMENTS

| | | | |
|---|---|---|---|
| 8,172,799 B2 | 5/2012 | Mohiuddin et al. | |
| 8,475,409 B2* | 7/2013 | Tsoukalis | A61M 5/14224 604/134 |
| 9,114,206 B2 | 8/2015 | Rader | |
| 9,480,791 B2 | 11/2016 | Reilly | |
| 9,700,672 B2 | 7/2017 | Capone et al. | |
| 2009/0112164 A1 | 4/2009 | Reilly et al. | |
| 2014/0031751 A1* | 1/2014 | Patrick | A61M 5/16827 604/131 |
| 2016/0051750 A1 | 2/2016 | Tsoukalis | |
| 2016/0256622 A1 | 9/2016 | Day et al. | |
| 2016/0331298 A1 | 11/2016 | Burnett et al. | |
| 2020/0060943 A1 | 2/2020 | Elia et al. | |

OTHER PUBLICATIONS

Applicant-Initiated Interview Summary dated Jan. 29, 2020 From the US Patent and Trademark Office Re. U.S. Appl. No. 16/110,016. (3 pages).
Final Official Action dated Oct. 8, 2020 from the US Patent and Trademark Office Re. U.S. Appl. No. 16/110,016. (14 pages).
International Preliminary Report on Patentability dated Mar. 4, 2021 From the International Bureau of WIPO Re. Application No. PCT/IL2019/050949. (13 Pages).
International Search Report and the Written Opinion dated Jan. 29, 2020 From the International Searching Authority Re. Application No. PCT/IL2019/050949. (22 Pages).
Invitation to Pay Additional Fees, Communication Relating to the Results of the Partial International Search and the Provisional Opinion dated Dec. 6, 2019 From the International Searching Authority Re. Application No. PCT/IL2019/050949. (17 Pages).
Notice of Allowance dated Dec. 8, 2020 from the US Patent and Trademark Office Re. U.S. Appl. No. 16/110,016. (11 pages).
Official Action dated Mar. 14, 2019 From the US Patent and Trademark Office Re. U.S. Appl. No. 16/110,016. (15 pages).
Official Action dated Oct. 22, 2019 From the US Patent and Trademark Office Re. U.S. Appl. No. 16/110,016. (34 pages).
Official Action dated Mar. 27, 2020 from the US Patent and Trademark Office Re. U.S. Appl. No. 16/110,016. (30 pages).
Restriction Official Action dated Jan. 9, 2019 From the US Patent and Trademark Office Re. U.S. Appl. No. 16/110,016. (8 pages).

* cited by examiner

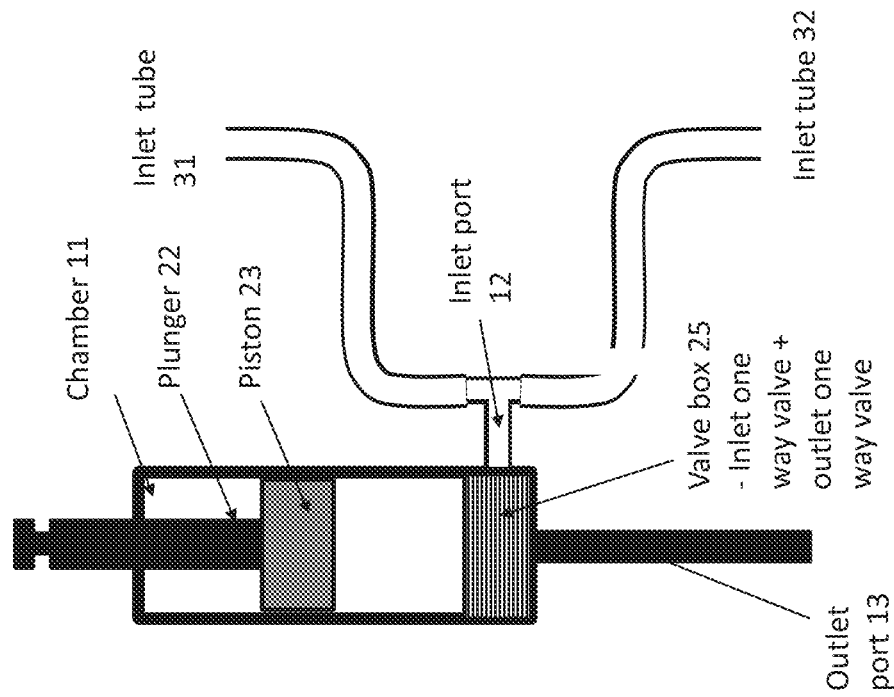
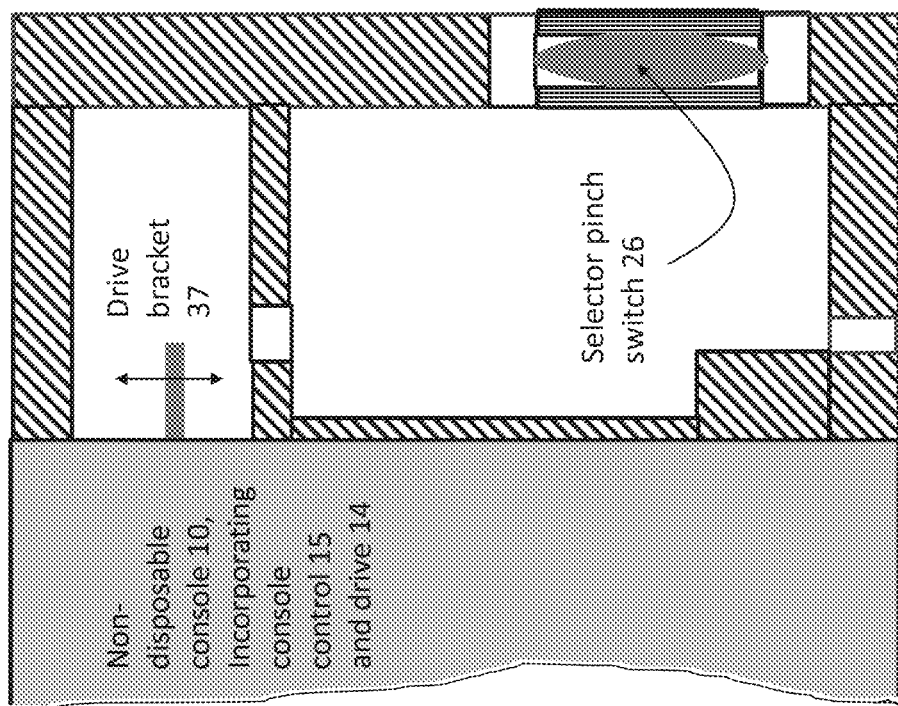
FIG. 2B

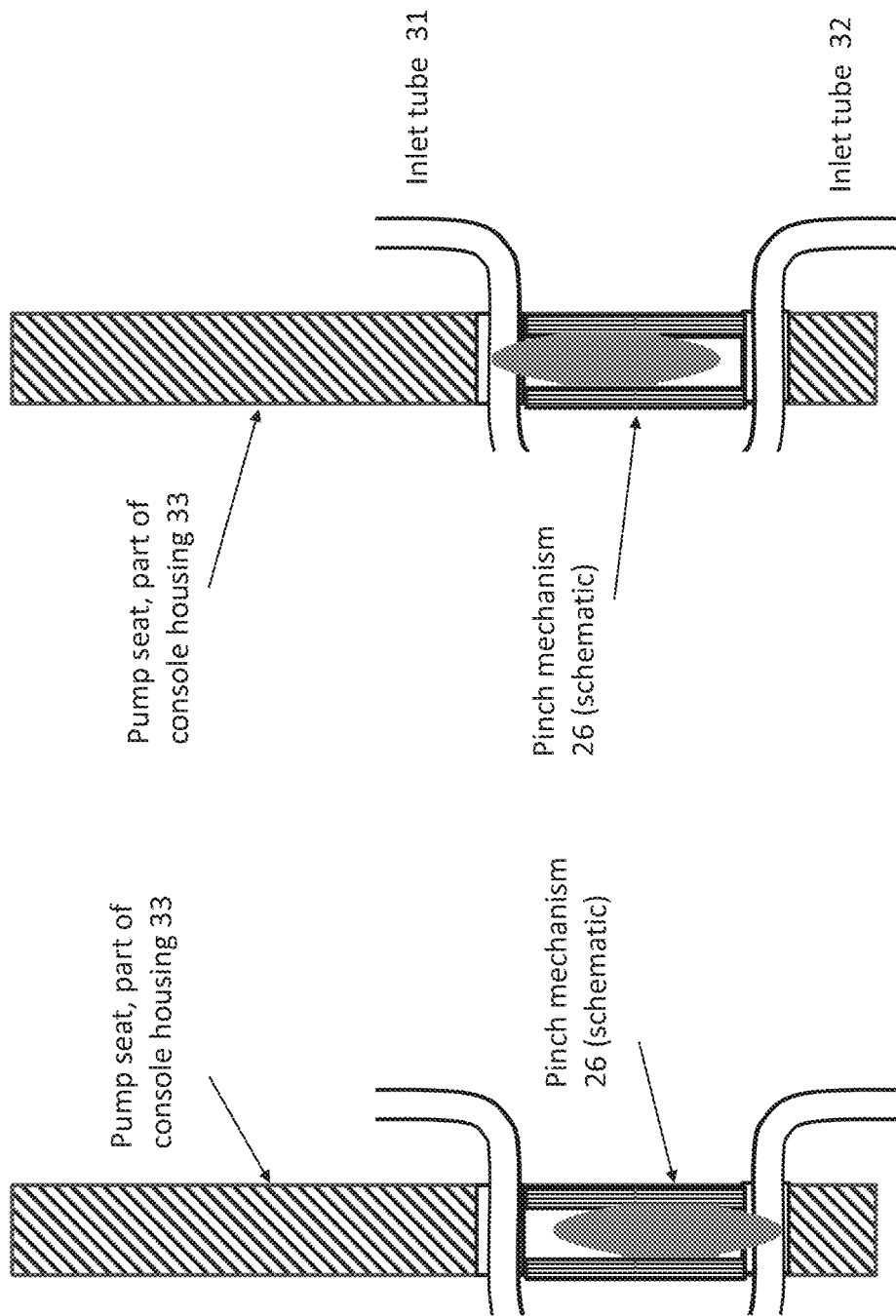

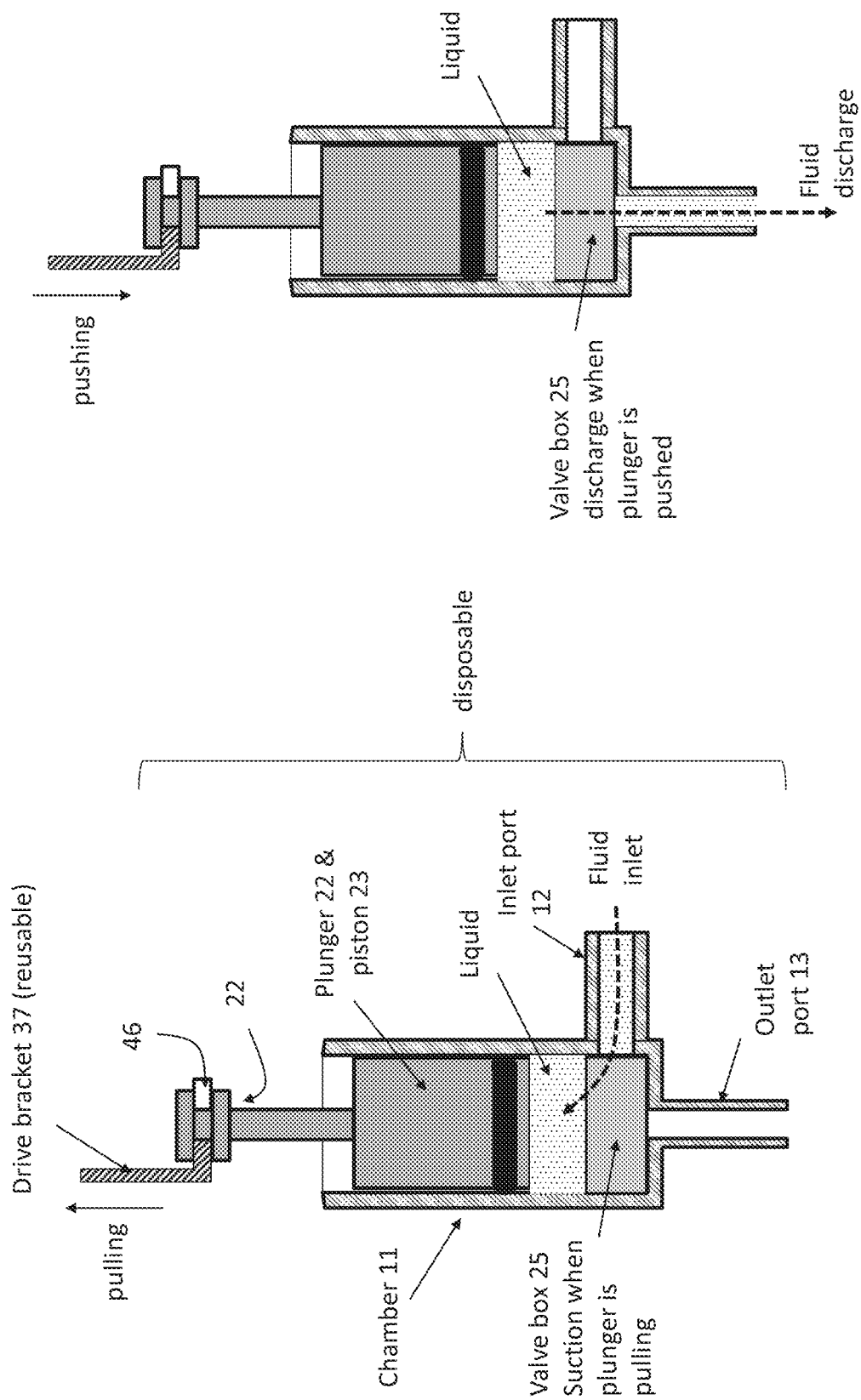

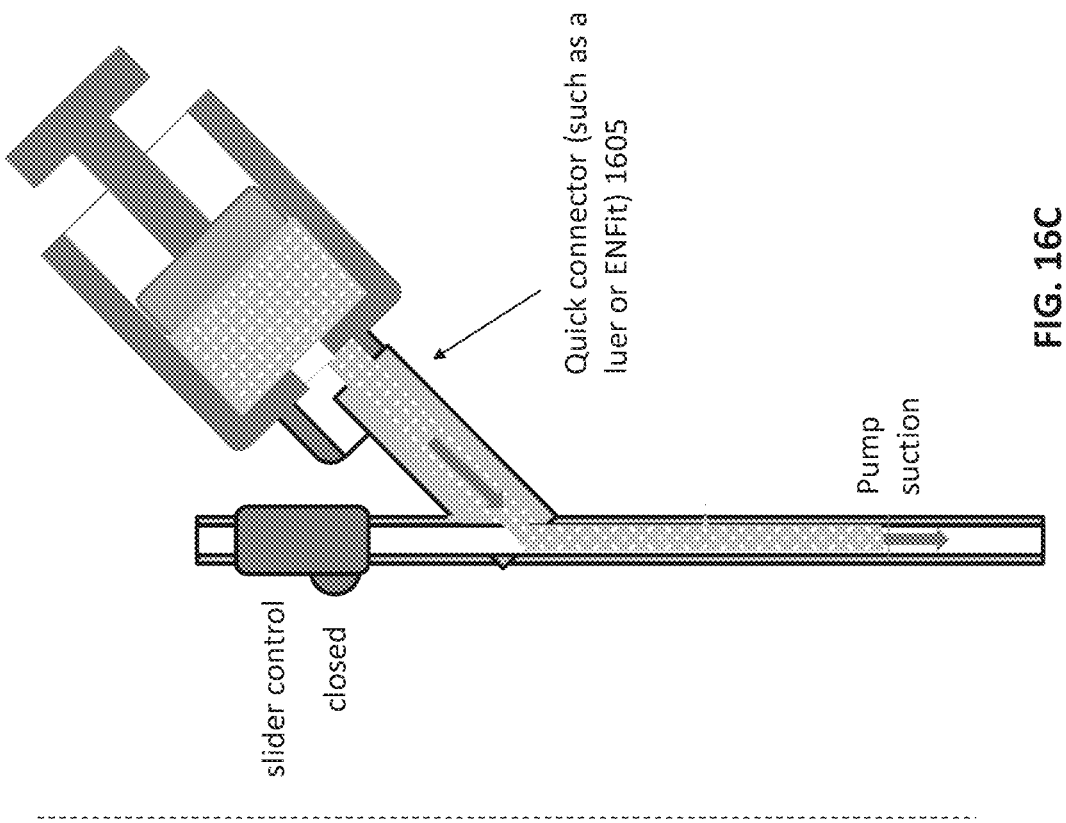
FIG. 16C
FIG. 16B
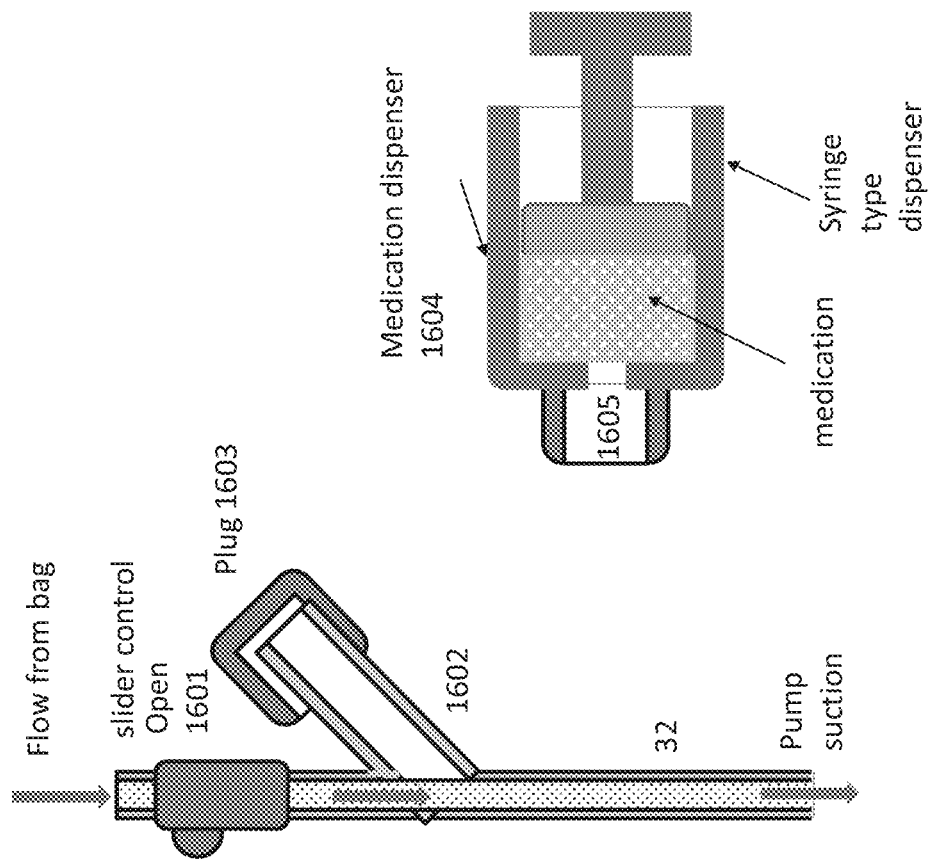
FIG. 16A

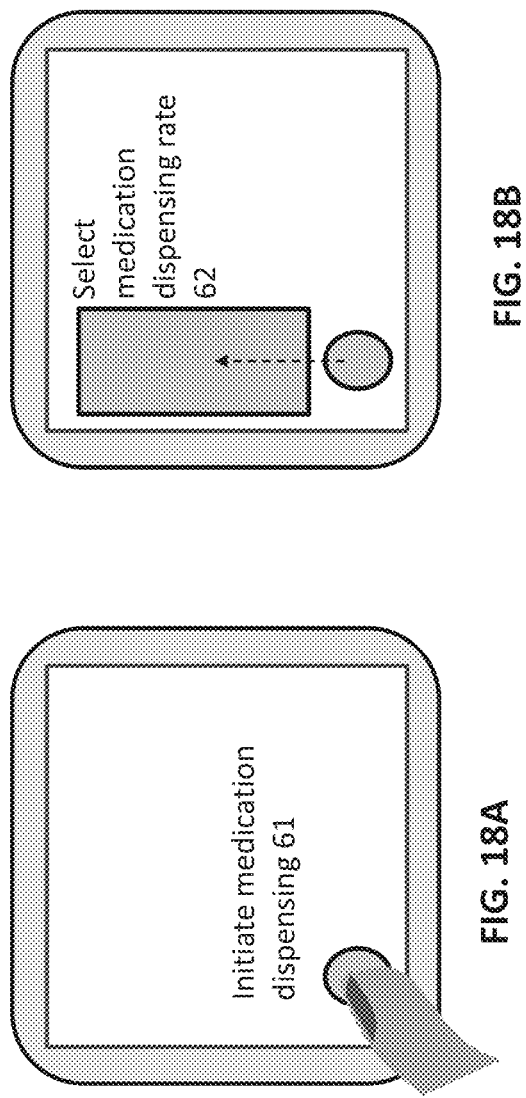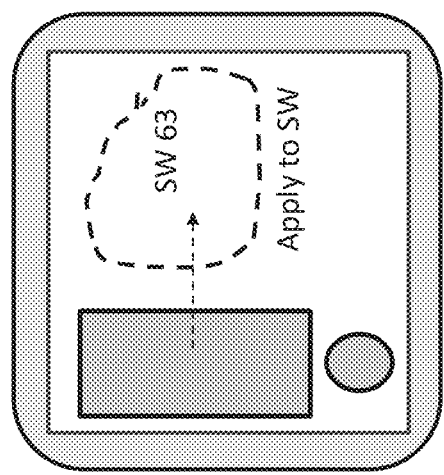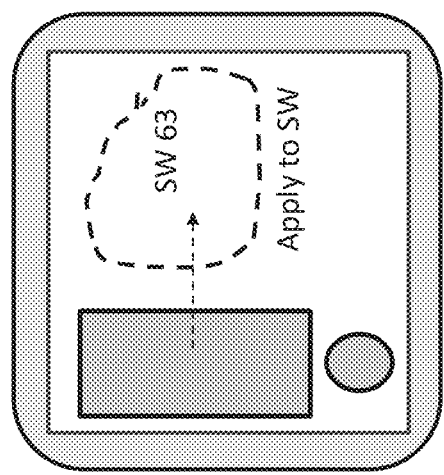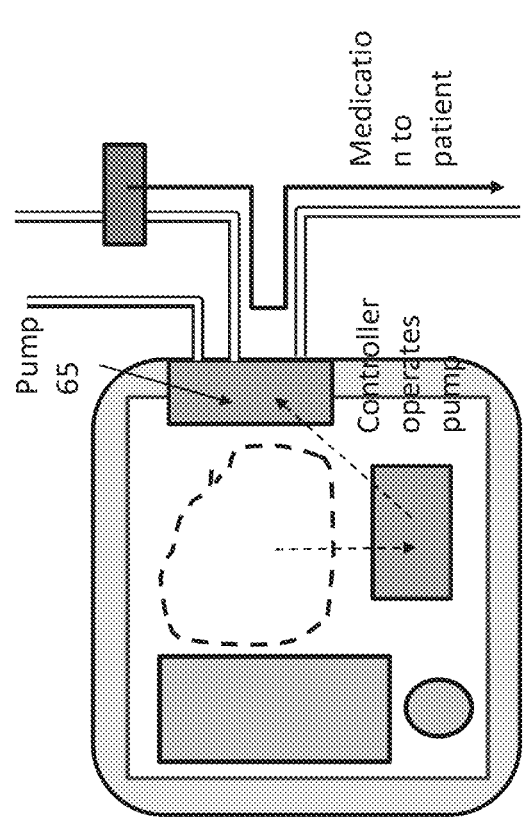

MEDICAL PUMP

RELATED APPLICATION

This application is a continuation of U.S. patent application Ser. No. 16/110,016 filed on Aug. 23, 2018, the contents of which are incorporated herein by reference in their entirety.

FIELD AND BACKGROUND OF THE INVENTION

The present invention, in some embodiments thereof, relates to a medical pump and, more particularly, but not exclusively, to structure, operation methodology and corresponding algorithms of a medical pump for continuously selecting and discharging multiple fluids.

Medical pumps are intensively used in the hospital and clinic environment for a long time, performing a variety of tasks such as assisting feeding patients, administering medications and rinsing.

In some of these applications, precision metering (exact flow rate control) is not critical while in other cases exact flow rate and as in the case of medication administration the total quantity is extremely critical. As a result of the large spectrum of specifications, large variety of medical pumps have been invented and are in production.

When dealing with feeding pumps most are based on peristaltic principle were a polygonal rotor is pushing fluids into a flexible tube. This current approach has a few disadvantages such as sensitivity to clogging and lack of sufficient accuracy, yet it is in use as it offers acceptable performance and incorporates low cost disposable parts that are in contact with the patient, thus avoiding the need to sterilize the pump.

In addition to the dispensing of food as described pumps are also used for dispensing water to the patient for several reasons such as: reducing the concentration of Sodium ($Na^+$) by water dilution and flushing the feeding tube in case of clogging.

Medication, when required, may be administered via the pump by crashing the solid agent to powder and mixing it with water to create a liquid phase or in some cases the medication is supplied as a liquid in the first place.

SUMMARY OF THE INVENTION

According to an aspect of some embodiments of the present invention there is provided a medical pump system, comprising: a fluid chamber having at least two intake openings, sealed by at least one intake valve, and an outlet opening sealed by an outlet valve; a piston which is sealing the fluid chamber and connected to a drive mechanism, the drive mechanism pulls the piston to draw fluid from one of the least two intake openings and pushes the piston to discharge the fluid into the outlet opening; and a selecting valve enclosing at least two tubes, each providing fluid to one of the at least two intake openings, wherein the selecting valve closes one of the at least two tubes while opening another of the at least two tubes.

Optionally, the drive mechanism is controlled by an electronic control unit.

Optionally, the selecting valve is controlled by an electronic control unit.

Optionally, at least one of the selecting valve, the at least one intake valve and the outlet valve is a one way valve.

Optionally, the selecting valve is instructed by an electronic control unit to alternately open and close the at least two tubes.

More optionally, the electronic control unit is connected to a display device, graphically displaying data related to operation of the medical pump system.

More optionally, the electronic control unit is connected to an electronic health record (EHR).

More optionally, the electronic control unit provides instructions which compensate for food losses due to gastric residual volume (GRV) and reflux feeding pause.

Optionally, the selecting valve is controlled using Pulse-width modulation (PWM) algorithm.

Optionally, the pump and the at least two tubes are disposable.

Optionally, the selecting valve is a pinch valve.

Optionally, the fluid chamber includes a cylinder.

Optionally, the piston is connected to the drive mechanism via a plunger rod having a slit which holds a reciprocating drive bracket of the drive mechanism and transfers reciprocal motion of the drive mechanism.

More optionally, the reciprocating drive bracket includes a fork type holder holding the slit.

Optionally, the drive mechanism is adjusted by an electronic control unit to administer a medication from a fluid dispenser connected to one of the at least two intake openings.

Optionally, one of the at least two tubes includes a fluid dispenser having a detachable fluid container.

Optionally, the at least two intake openings are connected into an intake channel.

Optionally, the at least one intake valve and the outlet valve are incorporated in a valve box.

According to an aspect of some embodiments of the present invention there is provided a fluid dispenser for a medical pump that may be attached to an inlet tube, comprising: a housing having an inlet opening, and an outlet opening connected to an intake opening of a medical pump; a piston enclosed in the housing, the piston having an inlet channel and a dispensing channel, wherein when the piston is in a released position, fluid flows from the inlet opening to the outlet opening via the inlet channel; and a detachable fluid container, wherein when the detachable fluid container is attached to the piston, the piston is moved to a pushed position and fluid flows from the detachable fluid container to the outlet opening via the dispensing channel.

According to an aspect of some embodiments of the present invention there is provided a method of controlling a medical pump, comprising: instructing a selecting valve enclosing at least two tubes, each providing fluid to one of a plurality of intake openings of a fluid housing, to close one of the at least two tubes while opening another of the at least two tubes; instructing a drive mechanism to pull a piston which is sealing the fluid chamber, the fluid chamber having the at least two intake openings and an outlet opening, to draw fluid from an open one of the least two tubes; and instructing the drive mechanism to push the plunger to discharge the fluid into the outlet opening.

According to an aspect of some embodiments of the present invention there is provided a method of preventing clogs in a feeding tube while feeding using a medical pump, comprising: pumping into a feeding tube at least one stroke of softening fluid, the at least one stroke of softening fluid fills a predetermined length of the feeding tube; pumping into the feeding tube at least one filling stroke of feeding fluid, so that the at least one stroke of softening fluid is pushed to a distal end of the feeding tube; pausing the pumping for a predetermined time to soften a clog in the distal end by the at least one stroke of softening fluid; and pumping into the feeding tube at least one flushing stroke of feeding fluid at a faster rate to remove the clog.

Optionally, the method further comprises pumping into the feeding tube a plurality of strokes of feeding fluid, so a total amount of the plurality of strokes of feeding fluid, the at least one filling stroke of feeding fluid and the at least one flushing stroke of feeding fluid during a feeding cycle is equal to a prescribed amount of feeding fluid for the feeding cycle.

Optionally, the method further comprises pumping into the feeding tube a plurality of strokes of softening fluid, so a total amount of the plurality of strokes of softening fluid and the at least one stroke of softening fluid during a feeding cycle is equal to a prescribed amount of softening fluid for the feeding cycle.

Optionally, the method further comprises detecting a rise in power consumption of a medical pump, indicating clogging of feeding fluid inside the feeding tube.

More optionally, the method further comprises pumping into the feeding tube a plurality of strokes of fluid at a faster rate to remove the clogging.

Optionally, the softening fluid is water.

Optionally, the predetermined length is between 5 and 15 centimeters.

Optionally, the predetermined time is at least 1 minute.

According to an aspect of some embodiments of the present invention there is provided a method for safe administration of medication, comprising: comparing prescription data of a medication to a patient stored by a terminal associated with the patient, with prescription data stored on a radio-frequency identification (RFID) device associated with a medication issued by a pharmacy; and when a match is found, instruction administration of the medication to the patient according to the data.

Optionally, the data includes at least one of medication type, dose, administration and patient ID.

Optionally, the terminal is stored at a bedside of the patient.

Optionally, the RFID device is attached to container of the medication.

According to an aspect of some embodiments of the present invention there is provided a disposable feeding set for a medical pump system, comprising: a fluid chamber having at least two intake openings, sealed by at least one intake valve, and an outlet opening sealed by an outlet valve; an outlet tube connected to the outlet valve; at least two intake tubes, each connected to one of the at least two intake openings; at least two fluid bags, each connected to one of the at least two intake tubes; a piston sealing the fluid chamber to be connected to a drive mechanism, the drive mechanism pulls the piston to draw fluid from one of the least two intake openings and pushes the piston to discharge the fluid into the outlet opening; and a selecting valve enclosing the at least two intake tubes, wherein the selecting valve closes one of the at least two intake tubes while opening another of the at least two intake tubes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A and 2B are schematic illustrations of a system comprising a disposable medical reciprocating pump, with the associated tubing, housed in a reusable console and outside the reusable console, respectively, according to some embodiments of the present invention;

FIGS. 4A and 4B are schematic illustrations of a non-disposable selector pinch switch when blocking inlet tube 1 and when blocking inlet tube 2, respectively, according to some embodiments of the present invention;

FIGS. 5A and 5B are schematic illustrations of a medical pump in suction action and discharge action, respectively, according to some embodiments of the present invention;

FIGS. 16A, 16B and 16C are schematic illustrations of a feed tube having a plug for a syringe type dispenser for a medical pump, a container of a syringe type dispenser and a syringe type dispenser connected to the tube via the plug, respectively, according to some embodiments of the present invention;

FIGS. 18A, 18B, 18C, 18D and 18E are schematic illustrations of an exemplary graphic user interface (GUI) used in operating the console, according to some embodiments of the present invention;

DESCRIPTION OF SPECIFIC EMBODIMENTS OF THE INVENTION

Figure 1:
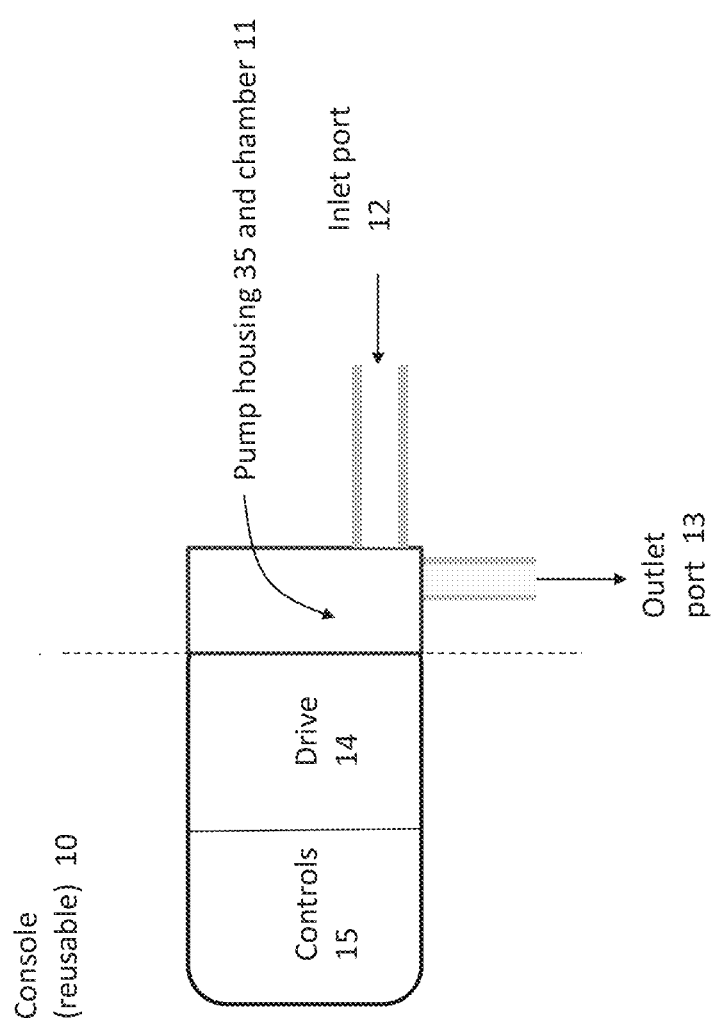
FIG. 1 is a schematic basic block diagram illustration of a medical pump, according to some embodiments of the present invention.

The present invention, in some embodiments thereof, relates to a medical pump and, more particularly, but not exclusively, to structure, operation methodology and corresponding algorithms of a medical pump for continuously selecting and discharging multiple fluids.

During enteral administration of food and/or other fluids, it is sometimes required to also administer water to the patient, to rinse the feeding line and for medical treatment requiring extra water. The common practice today includes adding, for example every hour or more, a bolus of 250 milliliter of water for the long term medical needs of the patient. It was observed that this practice of a large bolus administration may result patient reflux due to the sudden stomach loading which is highly undesirable.

A bolus of 250 ml that may be dispensed within minutes every several hours may result, for example in cases of hypernatremia, unnoticeable massive reflux that should be always avoided since it leads to aspiration pneumonia. Sensor equipped feeding tube is able to detect the undesired reflux.

Regarding the routine water flush to prevent tube clogging, in many cases this water dispensing practice is not able to flash out the clogging since the time interval between flashings results the hardening of the obstruction and the tubes are replaced every couple of days.

The medication administration has also shown to create undesired reflux since it may be administrated with a syringe of a 50 cc or 100 cc, for example, and again create reflux event.

Lately it has been shown that improving the accuracy of the feeding is essential to achieving nutritional goals and the specific feeding materials (caloric and protein) intake is directly related to faster recovery, shorter length of stay and reduced mortality rate.

Also, it has been shown that a single food selection is not the best choice for patient feeding and in some cases a mixed diet of two or more food agents yields better patient convalescence.

The proposed new invention teaches how to overcome these disadvantages of the current practice by offering a new pumping system and methodology which leads to much better patient feeding as dictated by the physician, by eliminating the disadvantages associated with the current systems, which also may not provide the actual feed rate as directed by the physician.

According to some embodiments of the present invention, there is provided a medical pump that receives two or more fluids from different sources such as bags or containers, and administers the fluids continuously according to a programmed administration plan and sensory readings handled by a controller processor attached to the pump. This is done by a selecting valve that select the flow from the tubes connected to the different fluid sources, such as fluid bags, and blocks some (usually one) of the tubes while opening another of the tubes for fluid flow. The selected valve is controlled by software that is implemented in a control unit of the pump, and may be adjusted by an operator via software.

Using the proposed medical pump, it is possible to precisely administer a small amount of each fluid, for example a few seconds, then change to another fluid, and repeat the process to achieve a continuous flow of a mix of the different fluids. For example, this enables a much safer approach to the water addition during feeding, by adding the needed water at a slower rate, avoiding undesirable sudden large boluses and thus preventing the danger of reflux.

Since the operation of the pump is controlled by software, this also allows administering accurate portions of each fluid based on sensory readings, enabling the completion of the daily feeding as instructed by the physician.

Optionally, the pump includes disposable manifold of inlet tubes, each of the tubes may be switched on or off by non-disposable switching valves, such as pinch switches (pinch valves), attached to the housing and not in contact with the fluid and the patient to avoid the need for cleaning or sterilization. The disposable manifold may be designed to be easily replaces and of low cost.

Optionally, the pump includes a reciprocating plunger which pulls the fluids from an intake opening(s) connected to the inlet tube that is currently selected and pushes it into an outlet opening which is connected by a tube to the patient via corresponding suction and discharge valves which are forming part of the disposable pump. This allows precision administration of the fluids by always transferring the same exact amount of fluid—the plunger stroke. Also, the positive displacement guarantees that clogs in the tubes are opened since the plunger is stiff and creates the pressure buildup (positive displacement) required to overcome the clog, which may also be monitored, for example, by electric current changes in the motor or pressure sensor. When there is a residual build-up, even before a full clog is created, the software detects current consumption increase and is able to take measures before a full clog is created.

When enteral feeding a patient, it is often required to administer medication in addition to the food and water that are commonly dispensed. The common practice of bolus dispensing water with the crashed medication or solution may result unwanted reflux, as described above. Therefore, it would be advantageous to administer the medication in small portions at a time.

According to some embodiments of the present invention, there is provided a feeding bag set that includes fluid bags, tubes, cylinder with plunger and piston and valve box.

According to some embodiments of the present invention, there is provided a dispenser that is connected to one of the tubes that are providing fluids to the pump, for example as part of the feeding bag kit. The medication is then dispensed from a fluid container of the dispenser by the operation of the pump. The control unit of the pump adjusts the pumping to a specific cycle that is desired for administering the medication. When medication session ends the pump resumes normal feeding and watering operation. Another embodiment is based on adding an extra medication bag and tube controlled by an additional switching valve.

The software-controlled switching of feeding, watering and medication administration in a gradual and intermitted schedule is important for the avoidance of reflux and may not be handled manually by a care taker.

According to some embodiments of the present invention, there is provided a method of avoiding clots at the distal end of a feeding tube, by pumping strokes of softening fluid, such as water, into the feeding tube, pumping strokes of feeding fluid that moves the softening fluid to the distal end of the feeding tube, pausing the pumping to let the softening fluid to soften the clog, and then pumping fast strokes of feeding fluid to flush the clog and softening fluid. This is done, for example, during each feeding cycle, and the amounts of fluids are calculated to fit the total amount of each fluid as prescribed by a physician.

The present invention presents a precision metering pump (reciprocating and disposable) with multiple selectable fluid inputs. These fluid inputs are software selectable with the aid of switching valves. Medication may be added by an attachment, container or via an extra bag in the feeding bag kit, controlled by a switch. An easy to mount mechanism may be integrated with the controller processor for the disposable pumping unit.

In addition, the software enables the compensation of lost feeding resulting from gastric residual volume (GRV) discharge and from pumping halt when reflux is sensed, both of which are detected by the system. The system has all the reflux data (i.e. the period of blocked feeding and the GRV/water and food losses) which is used as inputs for the software to compensate the daily feeding to the desired predetermined rates (calculated based on the Resting energy expenditure (REE) or Harris-Benedict equation and/or by any new regulations) as directed by the physician. The compensation may be arranged by increasing the next hour rate or by designing the daily feeding policy based on having non-active periods under undisturbed feeding, while the non-active periods may be used for the daily food intake compensation.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 2A:
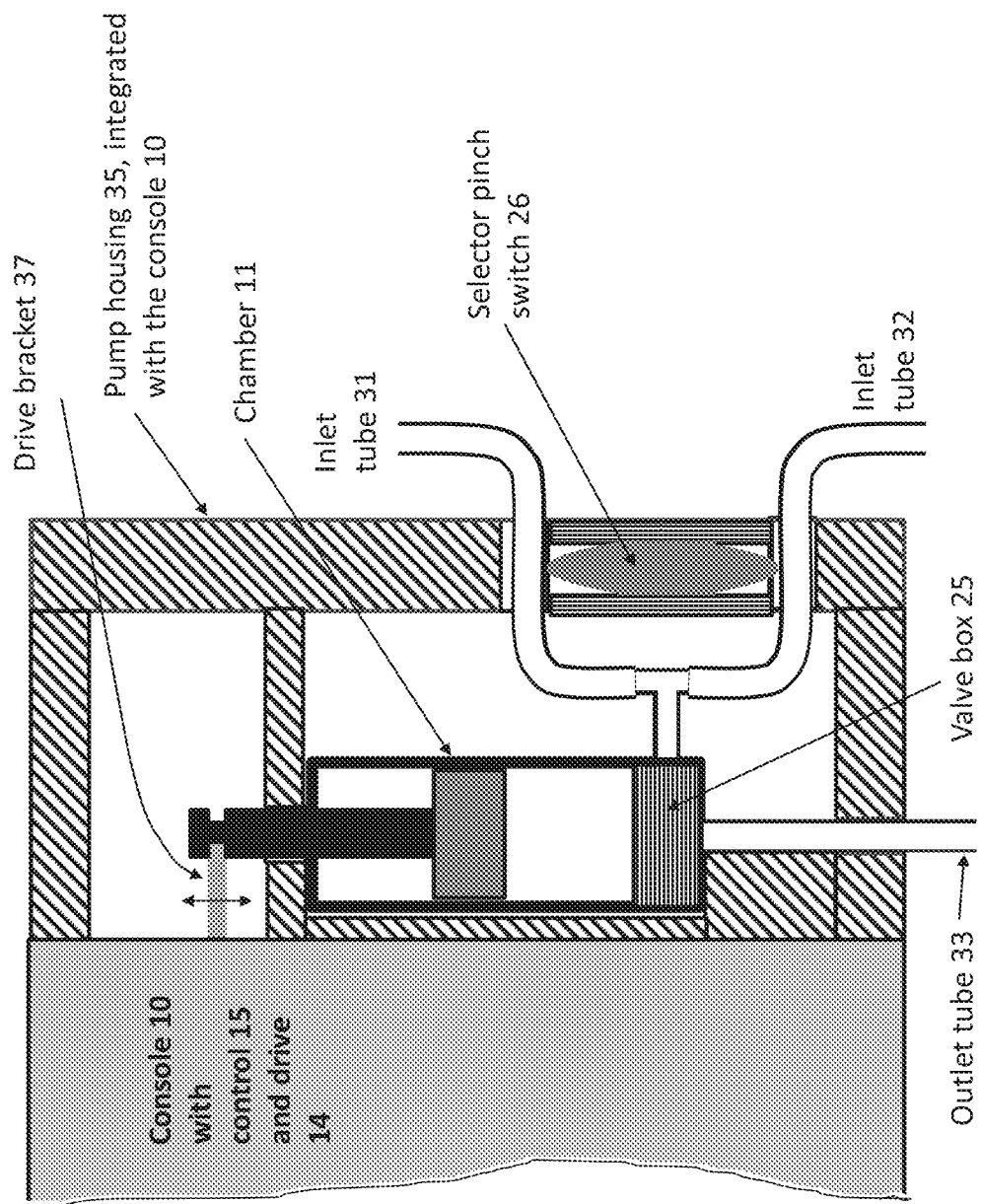

Referring now to the drawings, FIG. 1 is a schematic basic block diagram illustration of a medical pump, according to some embodiments of the present invention, emphasizing the separation into disposable system portion and no disposable (reusable) portion. Reference is also made to FIGS. 2A and 2B, which are schematic illustrations of a system comprising a disposable medical reciprocating pump, with the associated suction and discharge valve block, housed in a reusable console and outside the reusable console, respectively, according to some embodiments of the present invention.

The system includes a medical chamber 11, valve box 25 including inlet and outlet valves, a drive mechanism 14, a control unit 15 and the feed selector pinch switch 26 (a selecting valve).

Chamber 11 may be, for example, of a cylinder shape. The size of pump 24 may be, for example, 10 millimeters. Inlet feeding tubes 1 and 2 are opened by the selector pinch switch 26.

Console 10 includes the console control 15, the driving mechanism 14, housing 35 and the selector pinch switch 26. When disposable chamber 11 is mounted in the housing 35 of console 10, the drive bracket 37 is capable of pulling and pushing the plunger 22 thus performing the desired pumping action following commands (such as rate, stroke and duty cycle as described below).

Figure 3B:
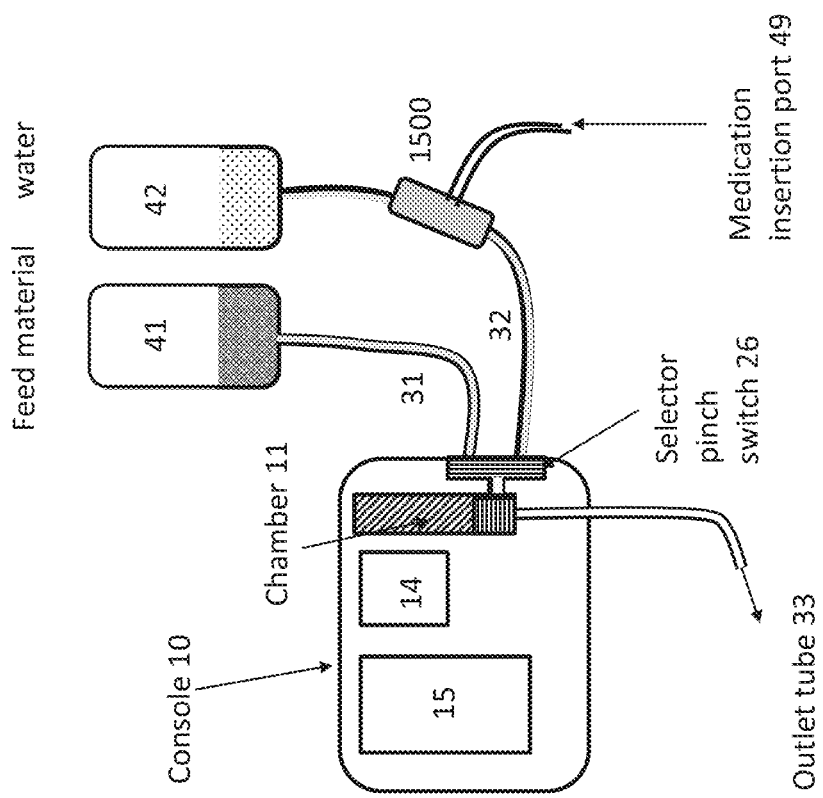
FIG. 3B is a schematic illustration of the system of 3A including a medication port, according to some embodiments of the present invention.
Figure 3A:
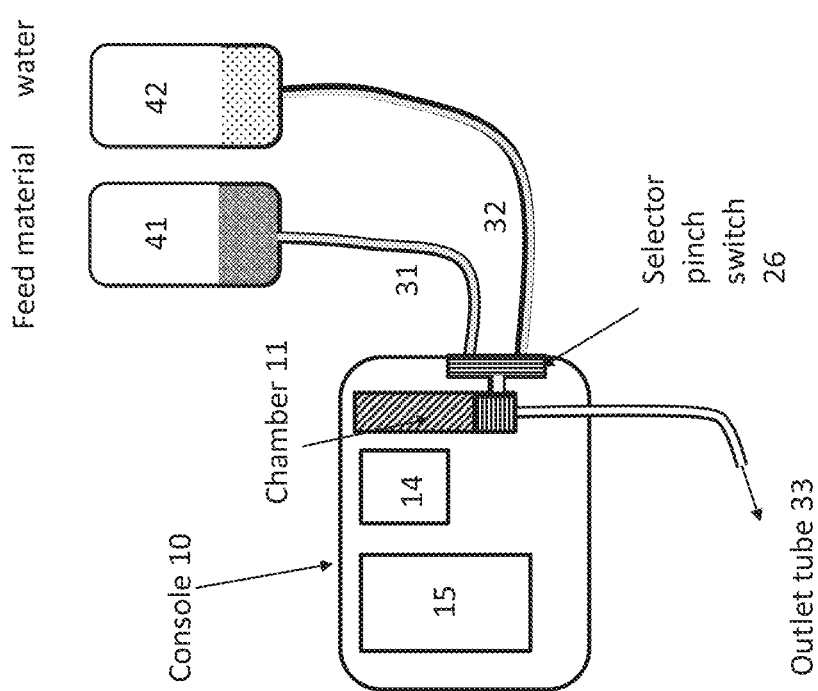
FIG. 3A is a schematic illustration of some aspects of a system including a disposable medical pump mounted inside a housing of a console, tubing and container bags, according to some embodiments of the present invention.

Reference is now made to FIG. 3A, which is a schematic illustration of some aspects of a system including a disposable medical chamber 11 mounted inside a housing 35 of a console 10, tubing and container bags of food 41 and water 42, according to some embodiments of the present invention. Reference is also made to FIG. 3B, which is a schematic illustration of the system of FIG. 3A including medication port 49, according to some embodiments of the present invention.

The chamber 11 is fed by at least two fluid bags and tubes 41, 42, selected by intake pinch valve 26, so that only the selected fluid may pass into the chamber 11 via inlet port 12 from the selected fluid bag. For example, fluid bag 41 is containing feed material and connected to tube 31, and fluid bag 42 is containing water and connected to tube 32. The fluid is then pumped through an outlet port 13 of the chamber 11 and via a tube to the patient. The fluids may be supplied in bags or special containers depending on vendor.

Optionally, one of the tubes, for example tube 32 is connected to a fluid dispenser, for example to administer a medication to the patient. FIG. 3B shows the addition of a medication port 49 as an option.

Reference is now made to FIGS. 4A and 4B, which are schematic illustrations of a non-disposable selector pinch switch 26 when blocking inlet tube 31 (FIG. 4A) and when blocking inlet tube 32 (FIG. 4B), according to some embodiments of the present invention. The non-disposable selector pinch switch 26 is part of console 10.

Reference is now made to FIGS. 5A and 5B, which are schematic illustrations of a medical pump in suction action and discharge action, respectively, according to some embodiments of the present invention.

Optionally, the intake valve(s) and/or the outlet valve are incorporated in a valve box 25. Valve box 25 may be, for example, of umbrella type, duckbill type, poppet type and/or any other type.

The fluid housing of chamber 11, for example cylinder 21, includes a plunger 22 (piston rod) and a piston 23 that is sealing cylinder 21 and performs reciprocating movement. Plunger 22 is connected to drive mechanism 14, which is controlled by control unit 15. Drive mechanism 14 pulls plunger 22 and piston 23, using drive bracket 37 to draw fluid from one of intake tubes 31 or 32 and pushes it to force the fluid via valve box 25 to the outlet port 13.

Optionally, plunger 22 is connected to drive mechanism 14 via a reciprocating drive bracket (or arm) 37 of drive mechanism 14. Optionally, plunger 22 includes a slit that transfers the reciprocal motion to drive bracket 37, for example via a fork shaped holder. This fork type design enables a quick mounting and removal of chamber 11 from console 10. Drive 14 may be constructed of an electric drive motor and a crank as is known in the art.

Optionally, chamber 11 and its associated tubing are parts of a disposable feeding bag set, and are detachable from console housing 35. Optionally, the chamber 11 and tubing are made of polymer materials, which allow low cost of the disposable part.

Figure 6:
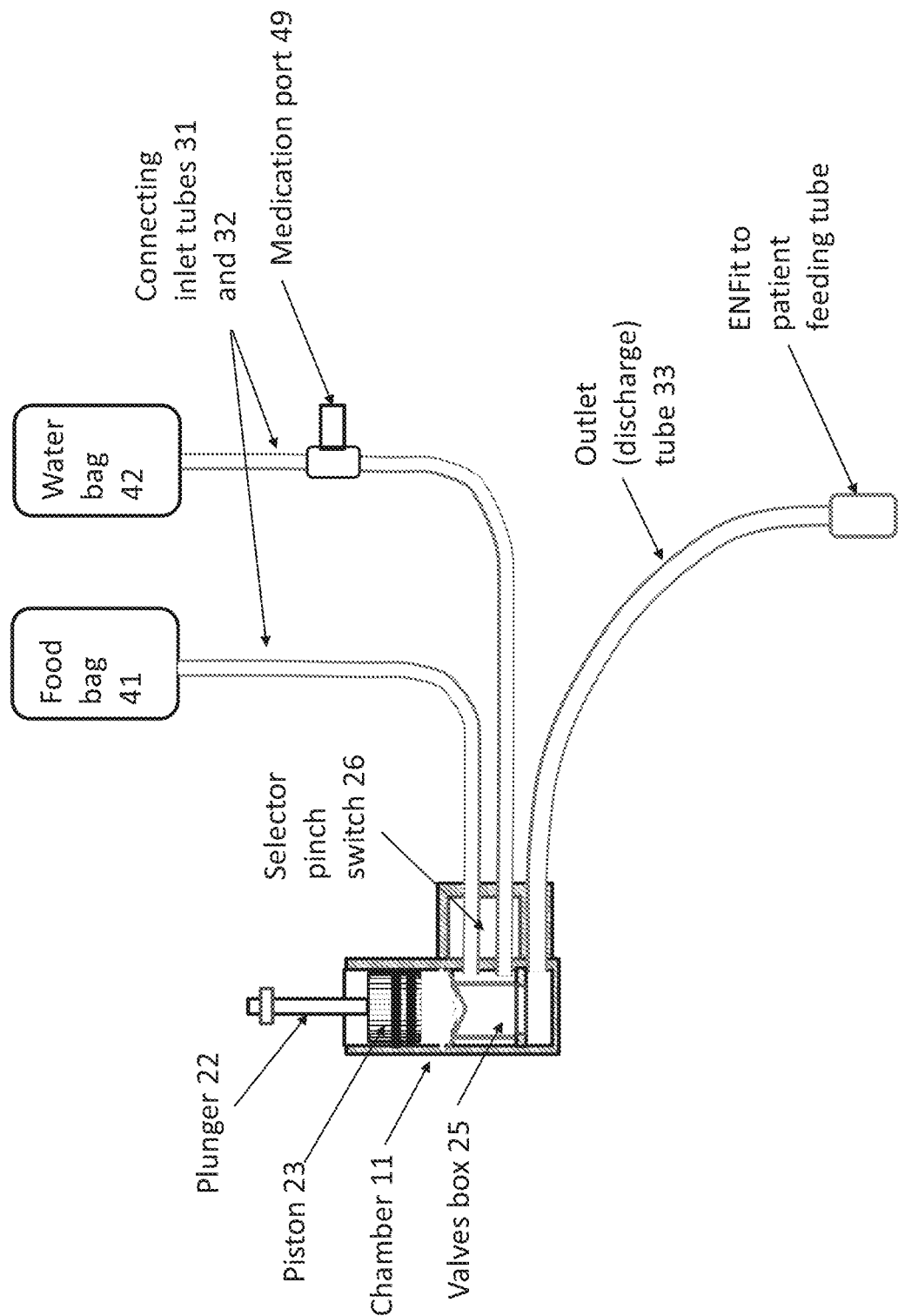
FIG. 6 is a schematic illustration of a disposable feeding bag set, according to some embodiments of the present invention

Reference is now made to FIG. 6, which is a schematic illustration of a disposable feeding bag set (assembly), according to some embodiments of the present invention. The disposable feeding bag set includes bags 41 and 42, tubes 31, 32 and 33, cylinder 21 with plunger 22 and piston 23, valve box 25 and optionally medication port 49.

An exemplary umbrella type valve box 25 is shown. When the plunger moves up the umbrella valve flips up, and the internal port of the umbrella valve is closed. Fluid may flow beneath the umbrella valve and suction is performed from active inlet. When the plunger moves down the umbrella valve flips down and the internal port of the umbrella valve opens.

Figure 7:
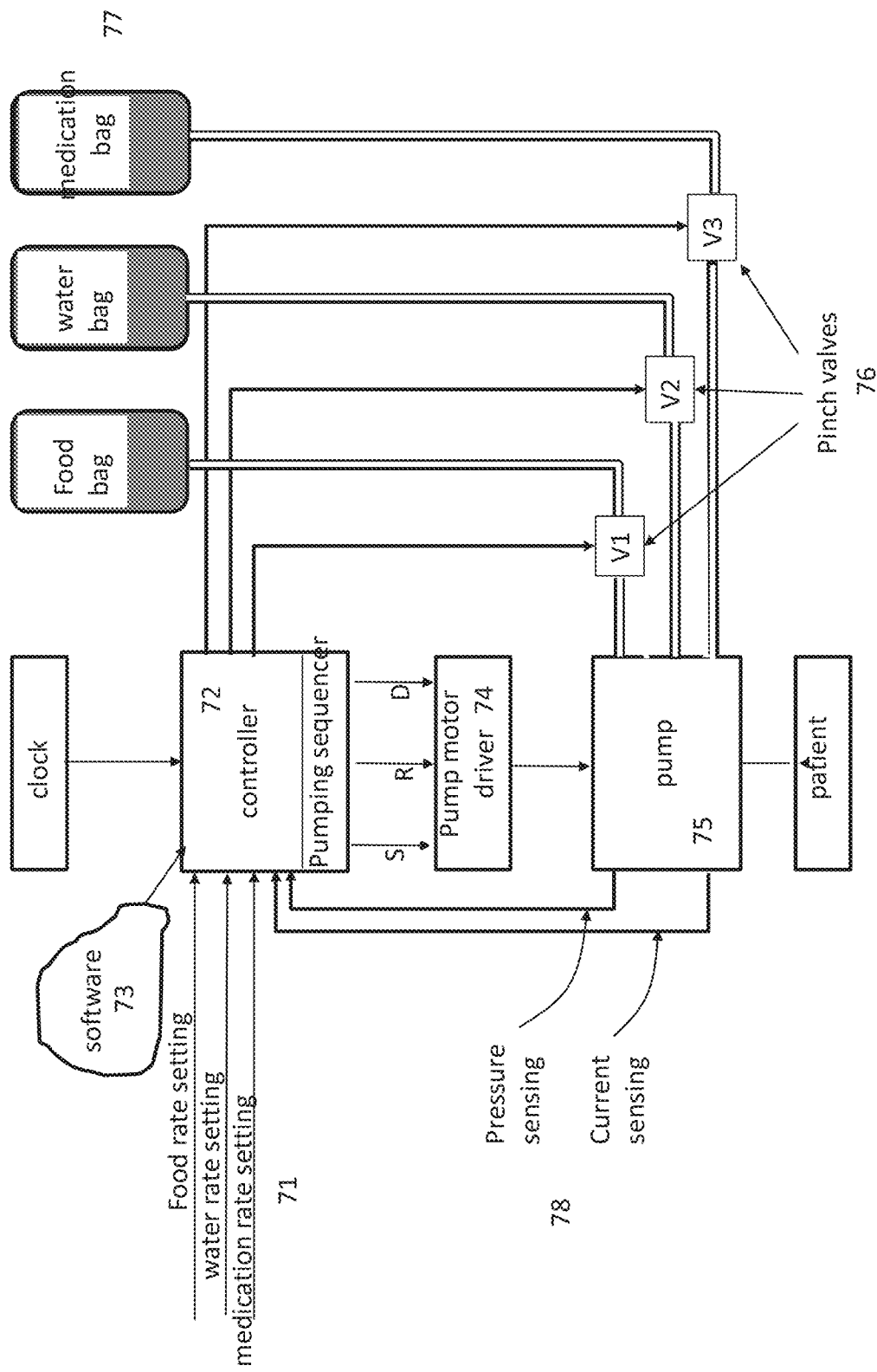
FIG. 7 is an overall block diagram schematically representing a method for controlling a medical pump, according to some embodiments of the present invention.

Reference is now made to FIG. 7, which is an overall block diagram schematically representing a method for controlling a medical pump, according to some embodiments of the present invention. In this embodiment, three fluid sources are presented with the corresponding software controlled selection pinch valves 76 (food, water, medication).

Command set 71 includes: food rate, water rate and medication rate settings. The command is transferred to the controller 72 operated by software 73 and activating the pump 75 via its driver 74. The system may include a smart feeding tube with reflux sensors and a GRV sensor which are used as input to the software and enable the compensation of feed losses due to GRV discharge and due to feed blocking when reflux is sensed.

Fluid bags 77 containing food, water and medication are connected to the pump through valves 76 (V1, V2, V3). 78 shows the pressure and current sensors that feed data to the pump controller as part of synthesis of the pump control signal.

Figure 8A:
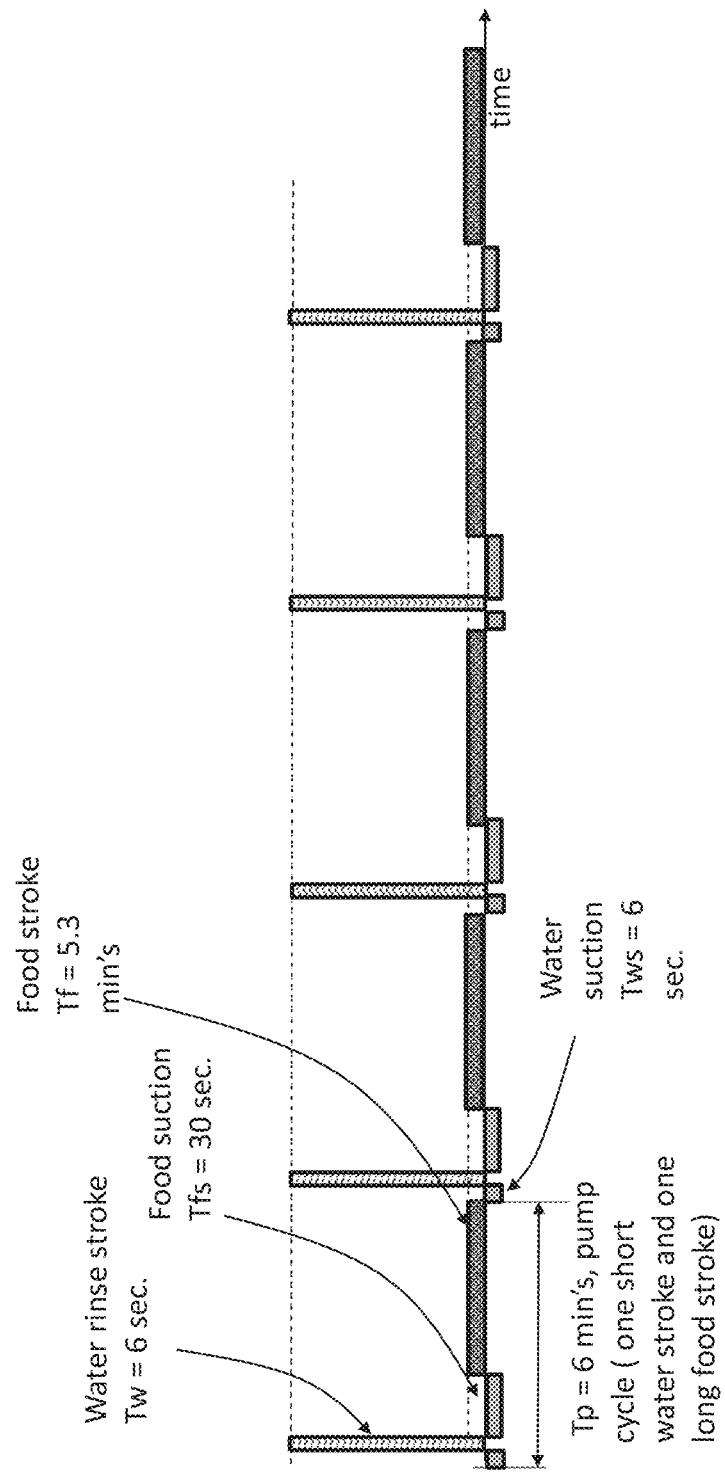
FIGS. 8A and 8B are exemplary pump drive pulse train timing diagrams, for food, water, and a medication stroke (7B), according to some embodiments of the present invention.
Figure 8B:
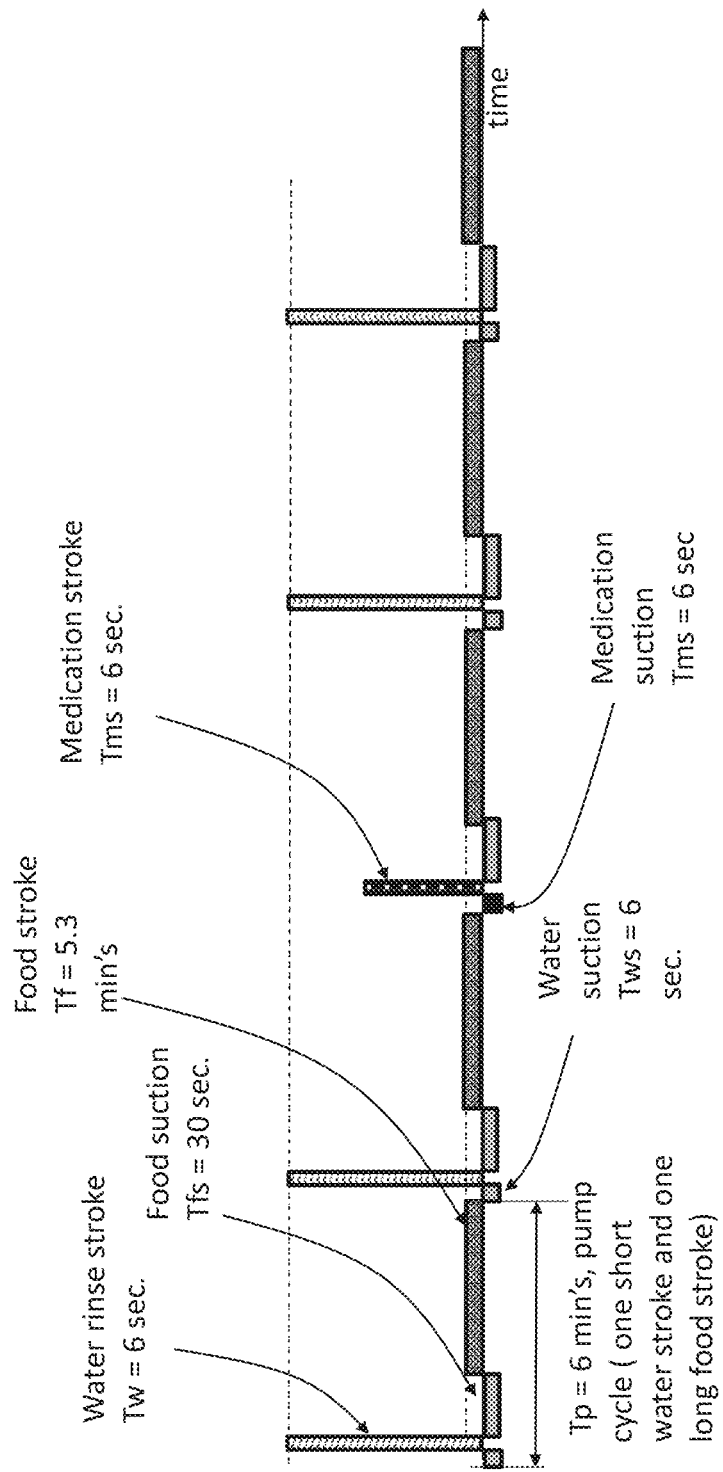

Reference is now made to FIGS. 8A and 8B, which are exemplary pump drive pulse train timing diagrams, according to some embodiments of the present invention. The diagrams show a 6 minute cycle which includes a single water suction and discharge phase and a single food suction and discharge phase. This pumping pulse train has a short water rinse pulse and a longer feed pulse. FIG. 7A also shows a medication administration phase.

Figure 9:
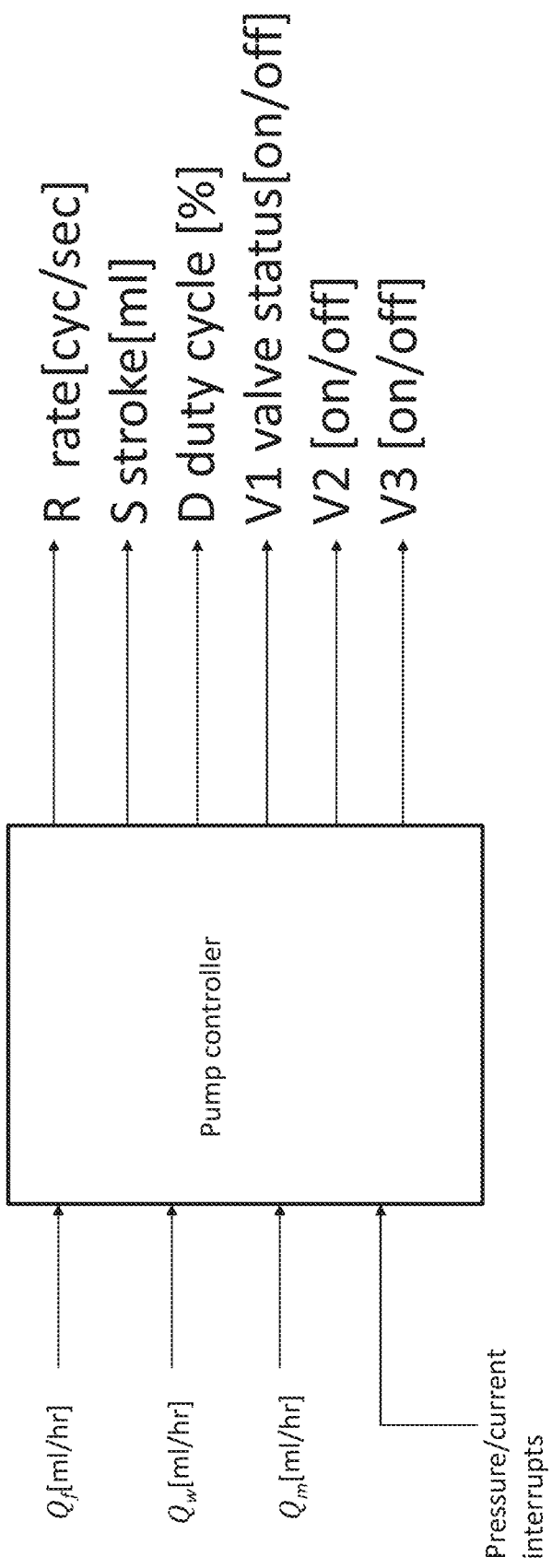
FIG. 9 is a block diagram showing pump controller typical inputs and outputs, according to some embodiments of the present invention.

Reference is now made to FIG. 9, which is a block diagram showing pump controller typical inputs and outputs, according to some embodiments of the present invention. The controller incorporates software that provides instructions for the system. The input set includes food rate Qf [milliliters per hour (ml/hr)] Qw [ml/hr] water rate and medication rate Qm [ml/hr]. The output set is resulting from the controller calculations, pump rate R [cycles per second], the stroke [ml], duty cycle [%] and valves status (V1,V2, V3). Optionally, when feeding has stopped for some intervals due to reflux as sensed by the reflux sensors or if food was lost due to GRV, the corresponding data is delivered to the software for calculating a compensation thus guaranteeing the proper daily feeding per physician decision.

Figure 10:
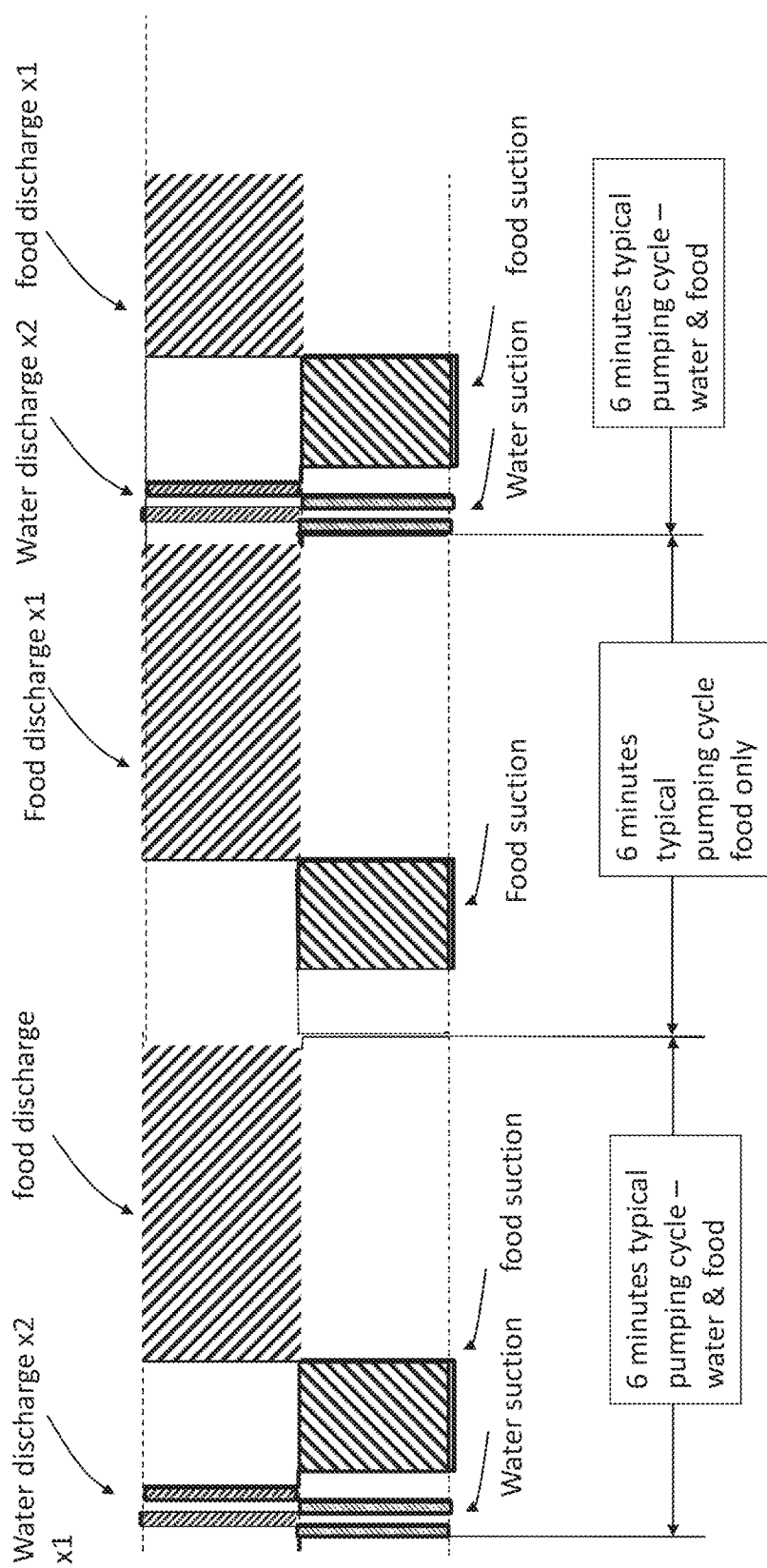
FIG. 10 is a numerical exemplary pump control pulse train timing diagrams with two water squirts per cycle, according to some embodiments of the present invention.
Figure 11:
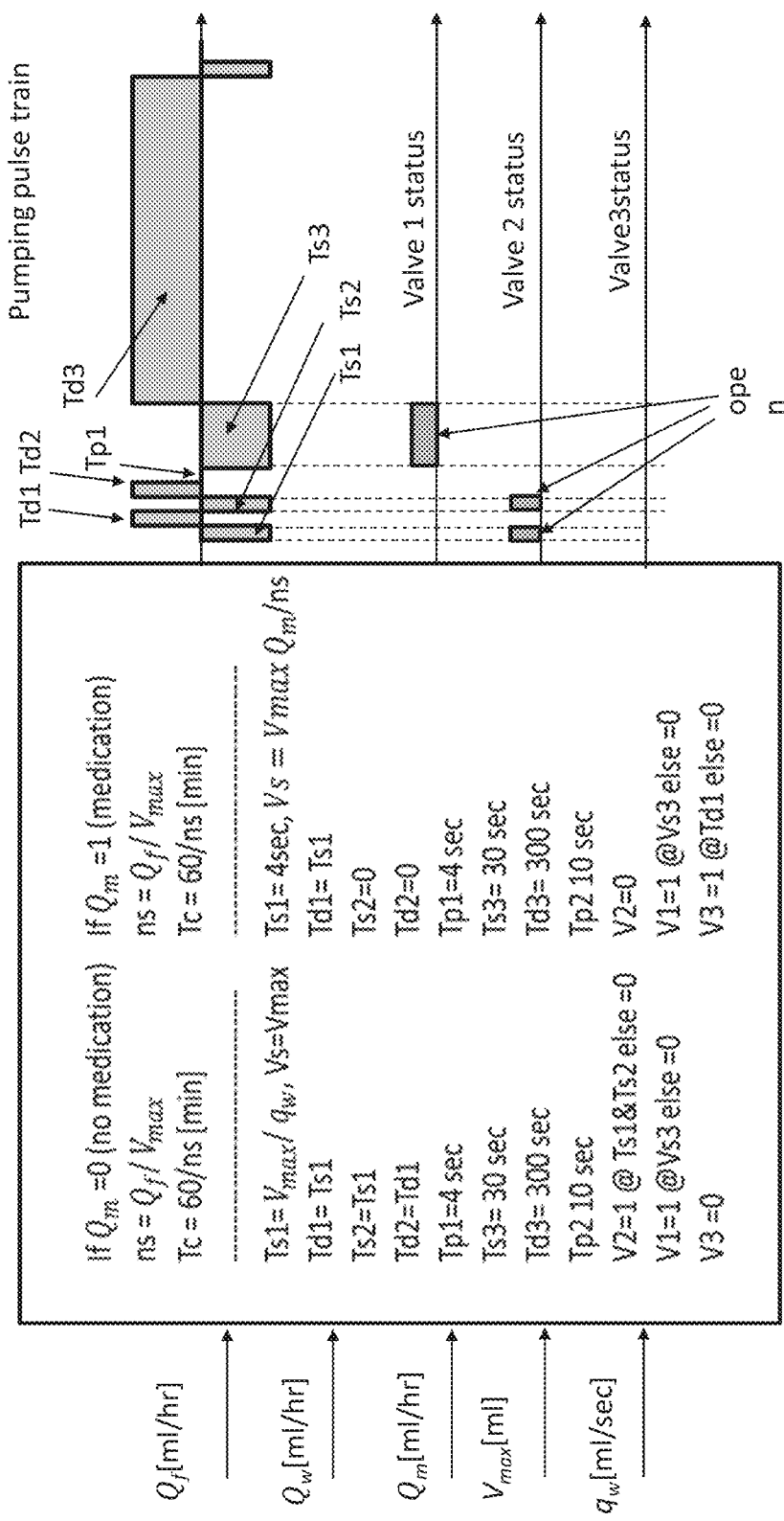
FIG. 11 is a block diagram showing a typical algorithm incorporating exemplary numerical values used for calculating the pumping and valving pulse train including pause sessions, according to some embodiments of the present invention.
Figure 12:
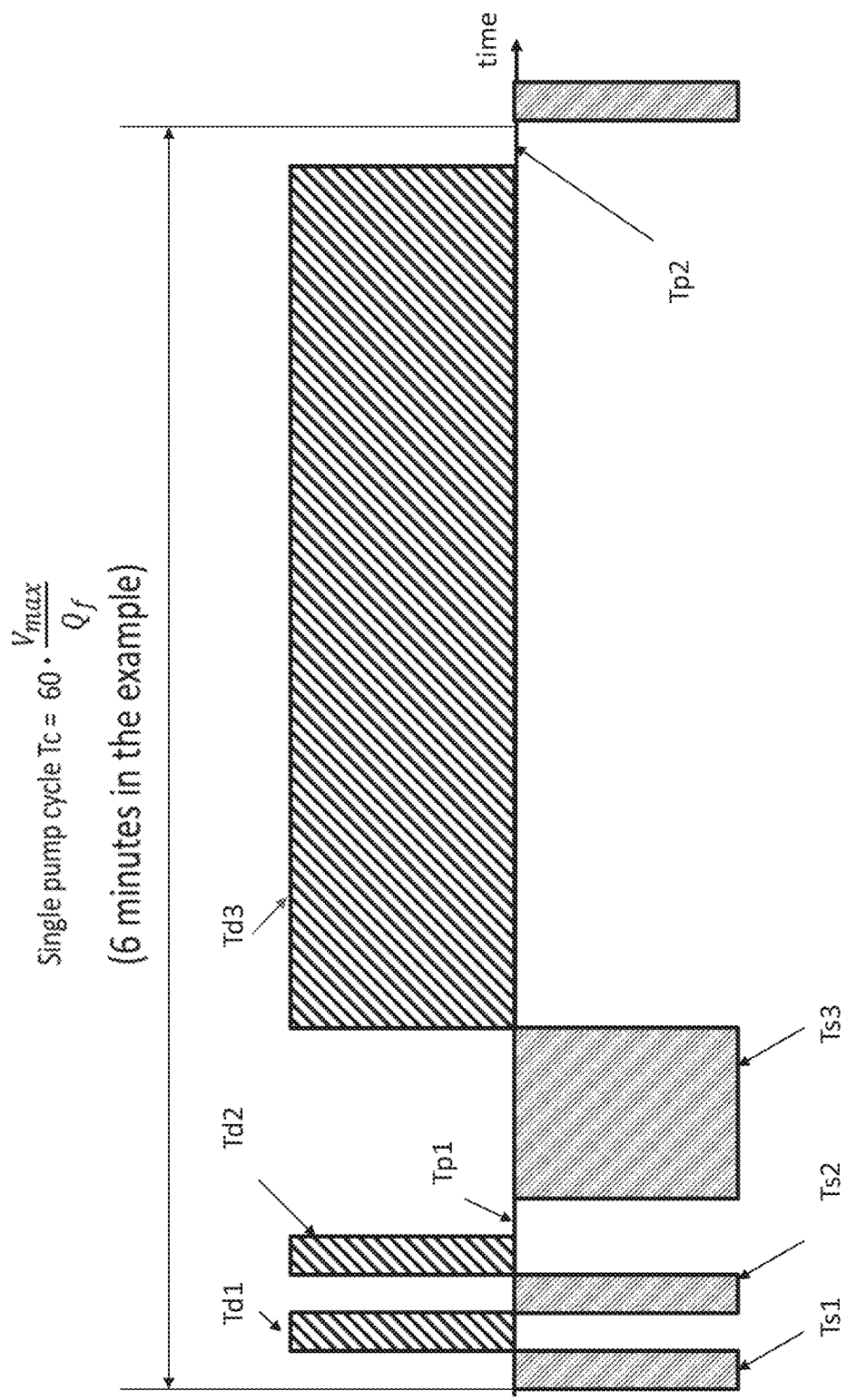
FIG. 12 is a detailed pump control pulse train timing diagrams of one cycle with parameters used for the pumping pulse train, according to some embodiments of the present invention.

Reference is now made to FIG. 10, which is a numerical exemplary pump control pulse train timing diagrams with two water squirts per cycle, according to some embodiments of the present invention. Reference is also made to FIG. 11, which is a block diagram showing a typical algorithm incorporating exemplary numerical values used for calculating the pumping and valving pulse train including pause sessions, according to some embodiments of the present invention. Reference is also made to FIG. 12, which is a detailed pump control pulse train timing diagrams of one cycle with parameters used for the pumping pulse train, according to some embodiments of the present invention. The algorithm is used for performing the calculations leading to the output parameters indicating the pump pulse train per cycle and the valves status. Two cases are described in FIG. 11. In the first no medication is required and in the sequel 1 ml/hr medication is required. The example indicates that each cycle is composed of two water squirts (each second cycle) followed by a slow feeding process. When medication is required it may be administered for example during the waterless cycle. Each water squirt takes 2 seconds for suction and 2 seconds for dispensing, followed by 4 seconds pause and the feeding which takes half a minute suction followed by 5 minutes dispensing the food. In total, the exemplary cycle shown lasts 6 min. Since the pump stroke in this example is 1.8 milliliters (ml) it leads to a feed rate of 60 ml/hr as required in the example. These figures are shown as an example, however other numerical values may result when the system parameters, such as the stroke volume, are different.

Figure 13A:
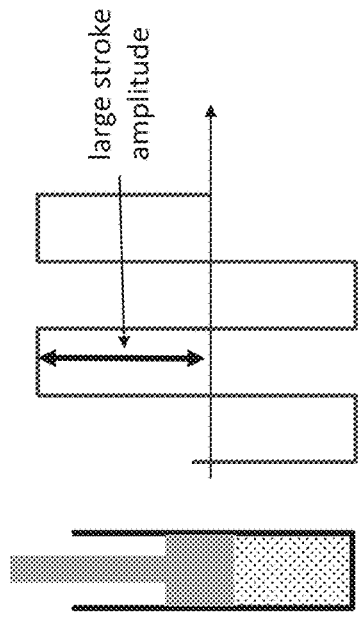
FIGS. 13A, 13B, 13C, 13D, 13E and 13F are schematic pump control pulse train timing diagrams showing the variables that are controlled by the algorithm, according to some embodiments of the present invention.
Figure 13B:
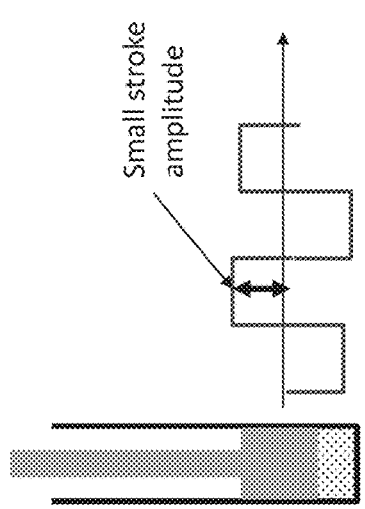
Figure 13C:
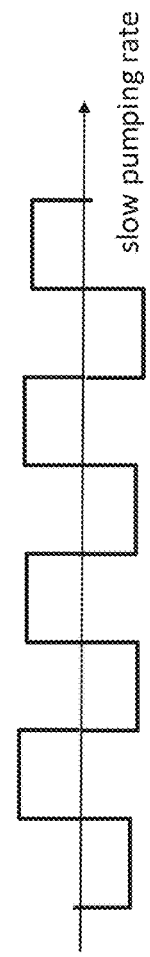
Figure 13D:
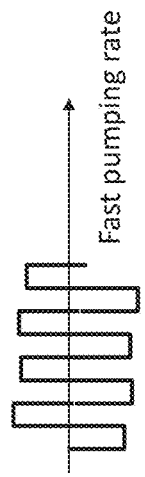
Figure 13E:
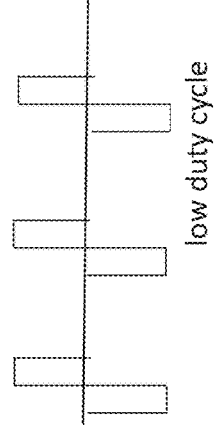
Figure 13F:
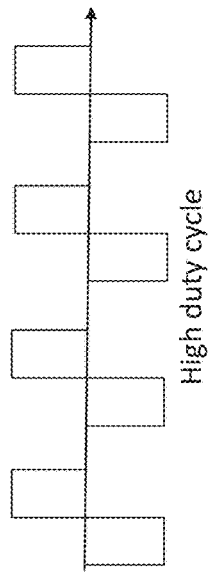

Reference is also made to FIGS. 13A, 13B, 13C, 13D, 13E and 13F, which are schematic pump control pulse train timing diagrams showing the variables that are controlled by the algorithm (stroke, frequency and duty cycle), according to some embodiments of the present invention. FIG. 13A and FIG. 13B demonstrate small stroke vs. large stroke, respectively. FIG. 13C and FIG. 13D demonstrate fast pumping rate vs. slow pumping rate, respectively. FIG. 13E and FIG. 13F demonstrate a high duty cycle vs. a low duty cycle, respectively.

Reference is also made to FIGS. 14A, 14B, 14C, 14D, 14E and 14F, which are schematic diagrams showing exemplary typical strokes and flow schedules for preventing clogs in a feeding tube while feeding using a medical pump, according to some embodiments of the present invention.

Figure 14B:
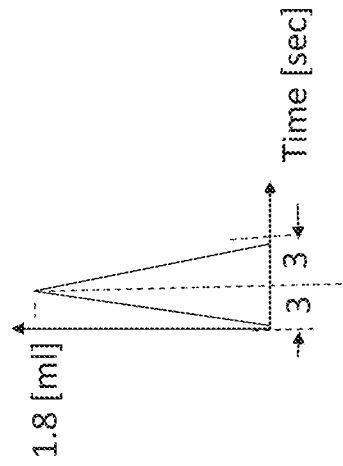
FIGS. 14A, 14B, 14C, 14D, 14E and 14F are schematic diagrams showing exemplary typical strokes and flow schedules for preventing clogs in a feeding tube while feeding using a medical pump, according to some embodiments of the present invention.
Figure 14C:
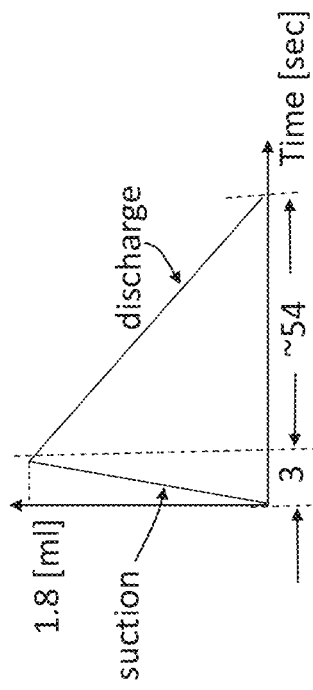
Figure 14A:
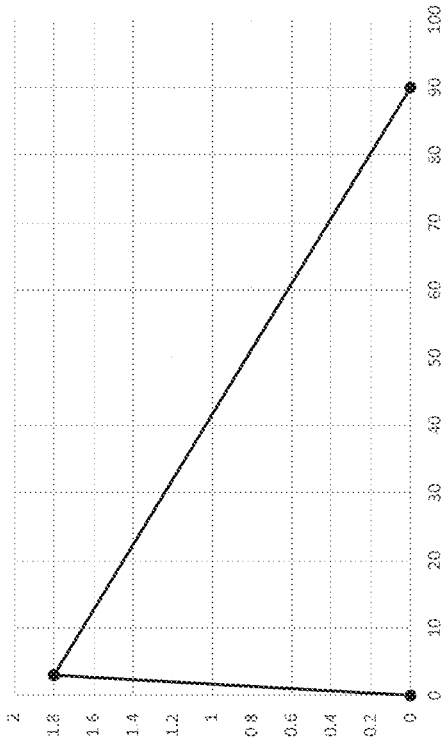

FIG. 14A and FIG. 14B show a typical stroke of fluid when it is pulled into the chamber from one of the intake tubes and then pushed out of the chamber into the outlet tube (feeding tube). For example, each stroke comprise of 1.8 ml of fluid. FIG. 14C shows a typical faster stroke of fluid.

Figure 14D:
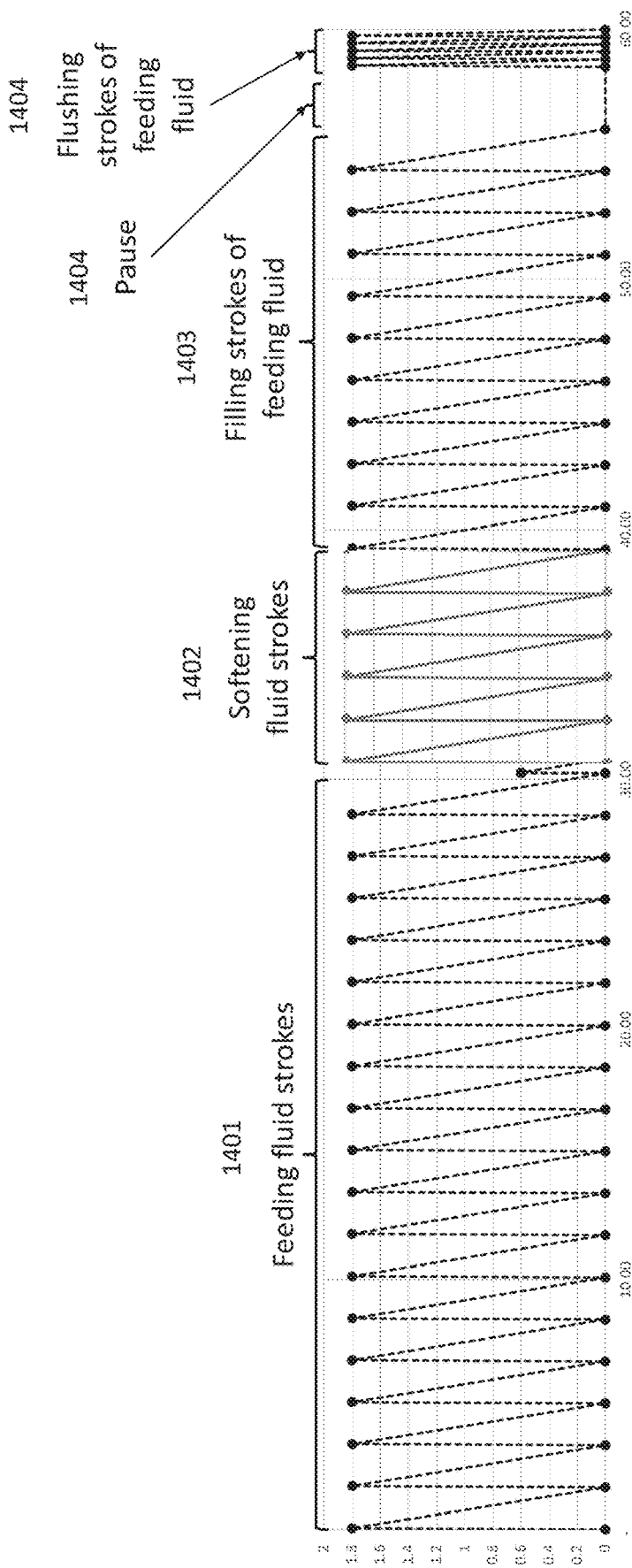

FIG. 14D shows an exemplary set of strokes during a one hour feeding cycle.

First, as shown at 1401, optionally, strokes of feeding fluid are pumped into the feeding tube to a patient.

Then, as shown at 1402, strokes of softening fluid, for example water, are pumped into the feeding tube, so they fill a predetermined length of said feeding tube (for example 5 strokes). The predetermined length is determined according to the structure of the feeding tube clog formation. The predetermined length may be for example 10 centimeters, between 5 and 10 centimeters, or any other length.

Then, as shown at 1403, filling strokes of feeding fluid are pumped into the feeding tube, so that the strokes of softening fluid are pushed to the distal end of the feeding tube, where clogs are usually formed. The amount of filling strokes of feeding fluid is determined by the length of the feeding tube, and together with the strokes of softening fluid should fill the feeding tube.

Then, as shown at 1404, the pumping is paused for a predetermined time to soften a clog in the distal end of the feeding tube by the softening fluid. The predetermined time may be, for example, 1 minute, 5 minutes, 10 minutes or any other smaller, larger or intermediate time.

Finally, as shown at 1405, flushing strokes of feeding fluid are pumped into the feeding tube at a faster rate to remove the softening fluid and the clog after it is softened by the softening fluid.

The amount of feeding fluid (and optionally water) that is pumped into the feeding tube at the first stage is calculated so that the total amount of feeding fluid during a feeding cycle is equal to a prescribed amount of feeding fluid for the feeding cycle, for example according to a medical direction by the physician. In this example, it is required to have a rate of 60 ml/hr of feeding fluid and a rate of 9 ml/hr of water, a total of 38 strokes of feeding fluid in a one hour cycle (for 1.8 ml stroke).

Figure 14E:
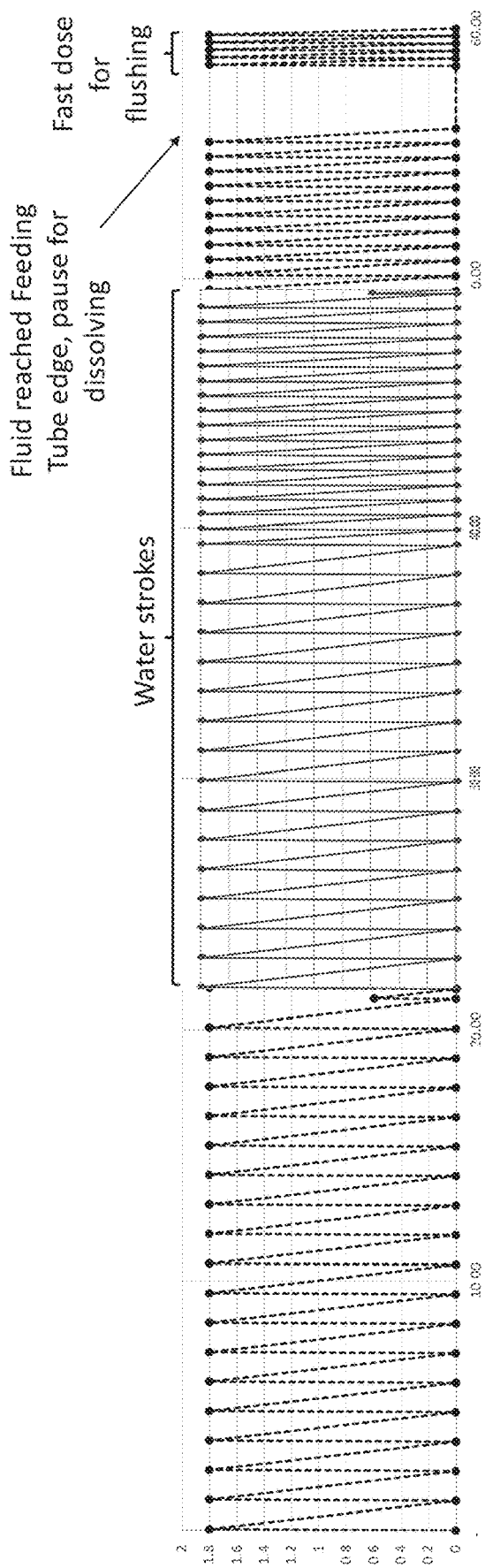

FIG. 14E shows another exemplary set of strokes during a one hour feeding cycle. In the described example it is required to have a rate of 60 ml/hr of feeding fluid (33.3 strokes) and a rate of 60 ml/hr of water (33.3 strokes) (the water flow rate may be determined, for example, according to a medical prescription by the physician). Water is pumped at nutrition rate until feeding tube empties from nutrition. Nutrition pumped at water speed until feeding tube emptied from fluid.

Figure 14F:
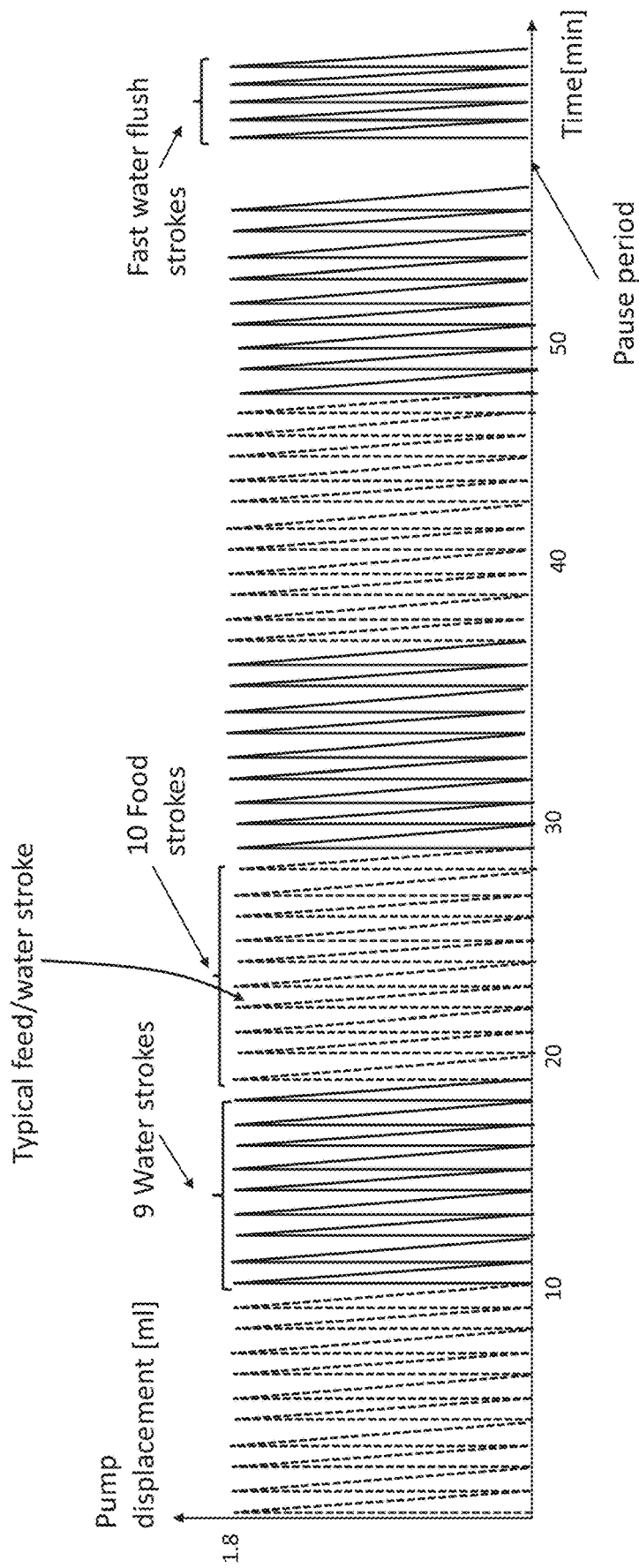

FIG. 14F shows another exemplary set of strokes during a one hour feeding cycle. In the shown example there are 30 food strokes of 1.8 ml, 27 water strokes of 1.8 ml and 5 fast water flush strokes of 1.8 ml. All strokes are done in a 60 minutes. The exemplary cycle is yielding a feeding rate of 54 ml/hr and water rate of about 57 ml/hr.

Figure 15:
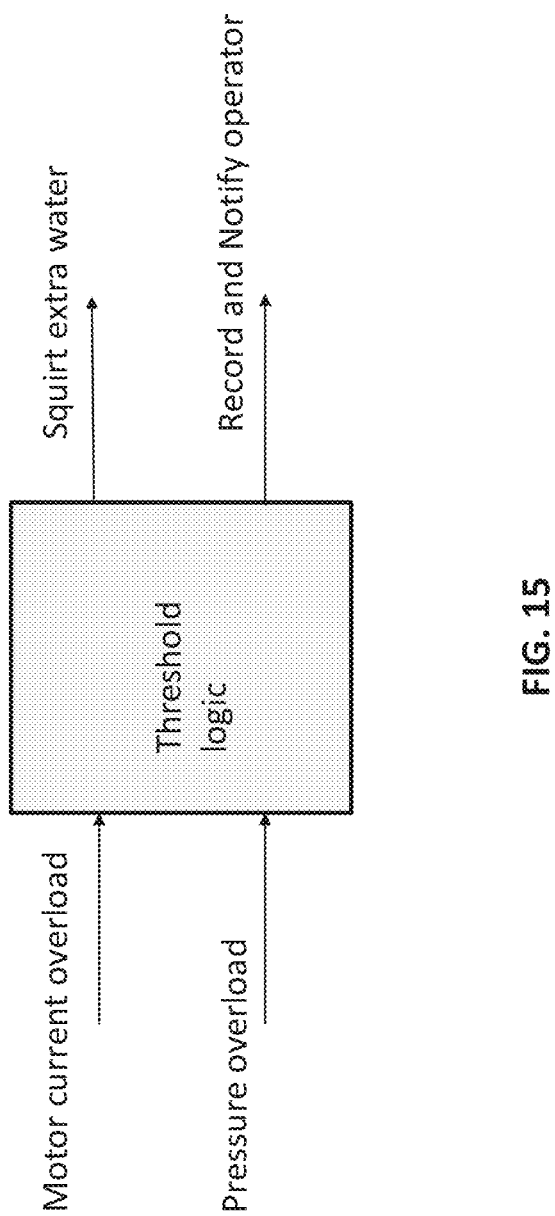
FIG. 15 is a block diagram showing flow obscuration logic management sensed and activated by motor overcurrent or over pressure, according to some embodiments of the present invention.

Reference is now made to FIG. 15, which is a block diagram showing flow obscuration logic management sensed and activated by motor overcurrent or over pressure, according to some embodiments of the present invention. A flow obscuration in the tube results in pump back pressure increase and/or drive current increase. This is detected, and an action is taken, for example speeding up the strokes of fluid, adding more water strokes or setting an alert for tube replacement.

In addition, the controller algorithm sets an alarm logic, which is not shown.

Reference is now made to FIG. 16A, FIG. 16B and FIG. 16C, which are schematic illustrations of a feed tube having a plug for a syringe type dispenser for a medical pump, a syringe type dispenser and a syringe type dispenser connected to the tube via the plug, respectively, according to some embodiments of the present invention.

Tube 32 includes a valve, such as a slide valve 1601, which closes tube 32 and prevents liquid flow from the liquid bag. Tube 32 also includes a dispensing opening 1602. Optionally, when in normal feeding process, opening 1602 is covered by a protection plug 1603. A fluid container 1604, for example a syringe-type fluid container, may be attached (and later detached when empty) to opening 1602 by a connector 1605 that allows fluid flow resulting from pump suction. The syringe is connected for example by a luer type coupling or ENFit type coupling.

An exemplary process of administering medication via a valve type dispenser is as follows:
1. Slide valve 1601 is closed to prevent liquid flow by an operator.
2. Pumping is halted. For example, the change in flow resistance is identified by control unit 15, which halts the pumping.
3. Fluid container 1604 is filled with the proper amount of medication by the operator.
4. Protection plug is removed by the operator.
5. Fluid container 1604 is coupled to the dispensing apparatus by connector 1605 by the operator.
6. The desired dispensing rate on the interactive screen is selected by the operator and inputted to control unit 15.
7. Pumping is resumed, for example automatically when a dispensing rate is selected by the operator.
8. Pumping is halted when the dispenser has been emptied. For example, the change in flow resistance is identified by control unit 15, which halts the pumping.
9. Syringe is removed and cup is installed by the operator.
10. Slid valve is reopened by the operator to enable fluid flow.
11. Pumping is resumed until the next medication schedule.

Reference is now made to FIG. 17A, FIG. 17B, FIG. 17C, and FIG. 17D, which are schematic illustrations of another embodiment based on a two-part fluid dispenser for a medical pump, according to some embodiments of the present invention.

The dispenser 1700 (also shown at FIG. 3B) includes a housing 1710 having an inlet opening 1711 which is connected to an inlet tube that provides fluid, and an outlet opening 1712 which is connected to an intake opening of a medical pump, for example intake opening, via a tube such as tube 32.

A piston 1720 is enclosed in housing 1710. Piston 1720 includes an inlet channel 1721 and a dispensing channel 1722. Housing 1710 may include a stopper pin 1715 to prevent piston 1720 from sliding out of housing 1710.

When piston 1720 is in a released position, fluid flows from inlet opening 1711 to outlet opening 1712 via inlet channel 1721.

The dispenser also includes a detachable fluid container 1730, for example a container of medication. Detachable fluid container 1730 may be attached to piston 1720, for example via a connector 1731 that allows fluid flow, for example a luer type coupling or ENFit type coupling. When detachable fluid container 1730 is attached to piston 1720, piston 1720 is moved to a pushed position and fluid flows from detachable fluid container 1730 to outlet opening 1712 via dispensing channel 1722. In pushed position, piston 1720 is pushed against a spring 1714, thus blocking the flow from the fluid bag through inlet channel 1721 and enabling flow from detachable fluid container 1730 via the dispensing channel 1722. Optionally, when in normal feeding process, housing 1710 is sealed by a protection plug 1713, so dispensing channel 1722 is closed.

When Detachable fluid container 1730 is detached from piston 1720, spring 1714 pushes piston 1720 back to a released position, thus enabling fluid flow from the fluid bag via inlet channel 1721.

Figure 17B:
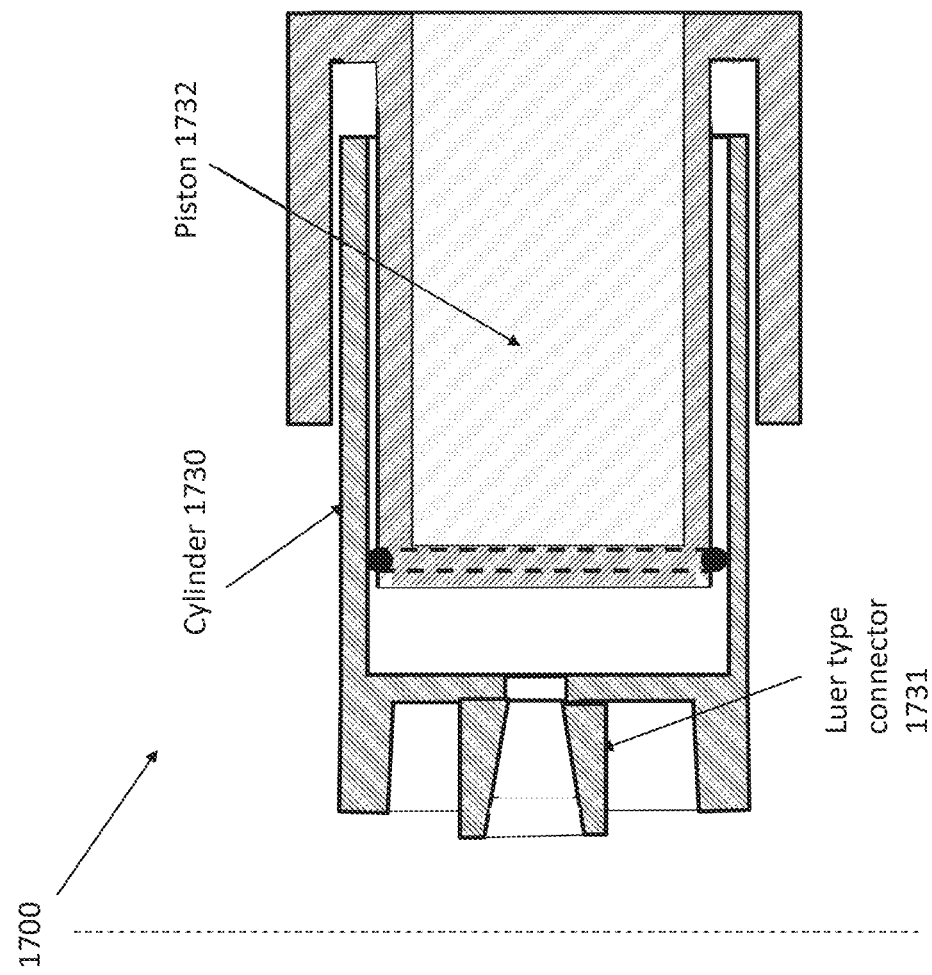
FIGS. 17A, 17B, 17C and 17D are schematic illustrations of another embodiment based on a two-part fluid dispenser for a medical pump, according to some embodiments of the present invention.
Figure 17A:
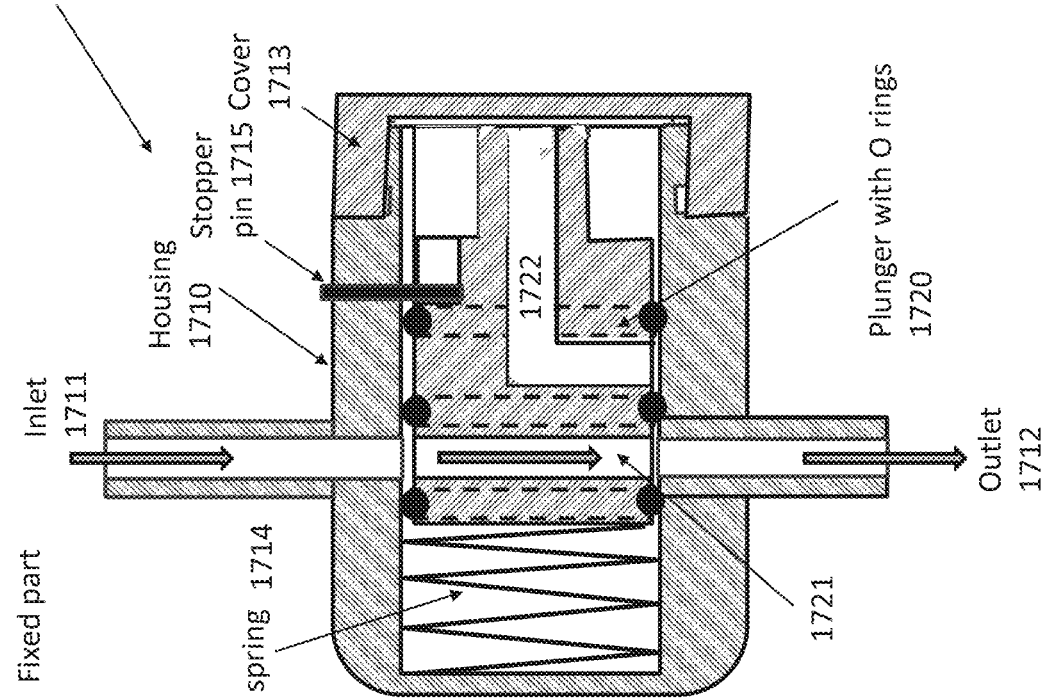
Figure 17C:
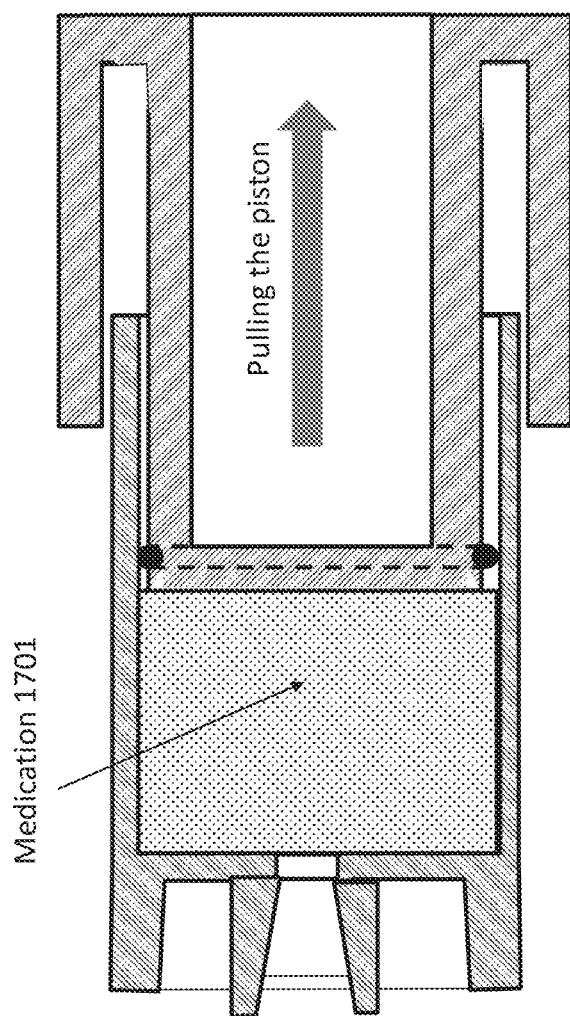
Figure 17D:
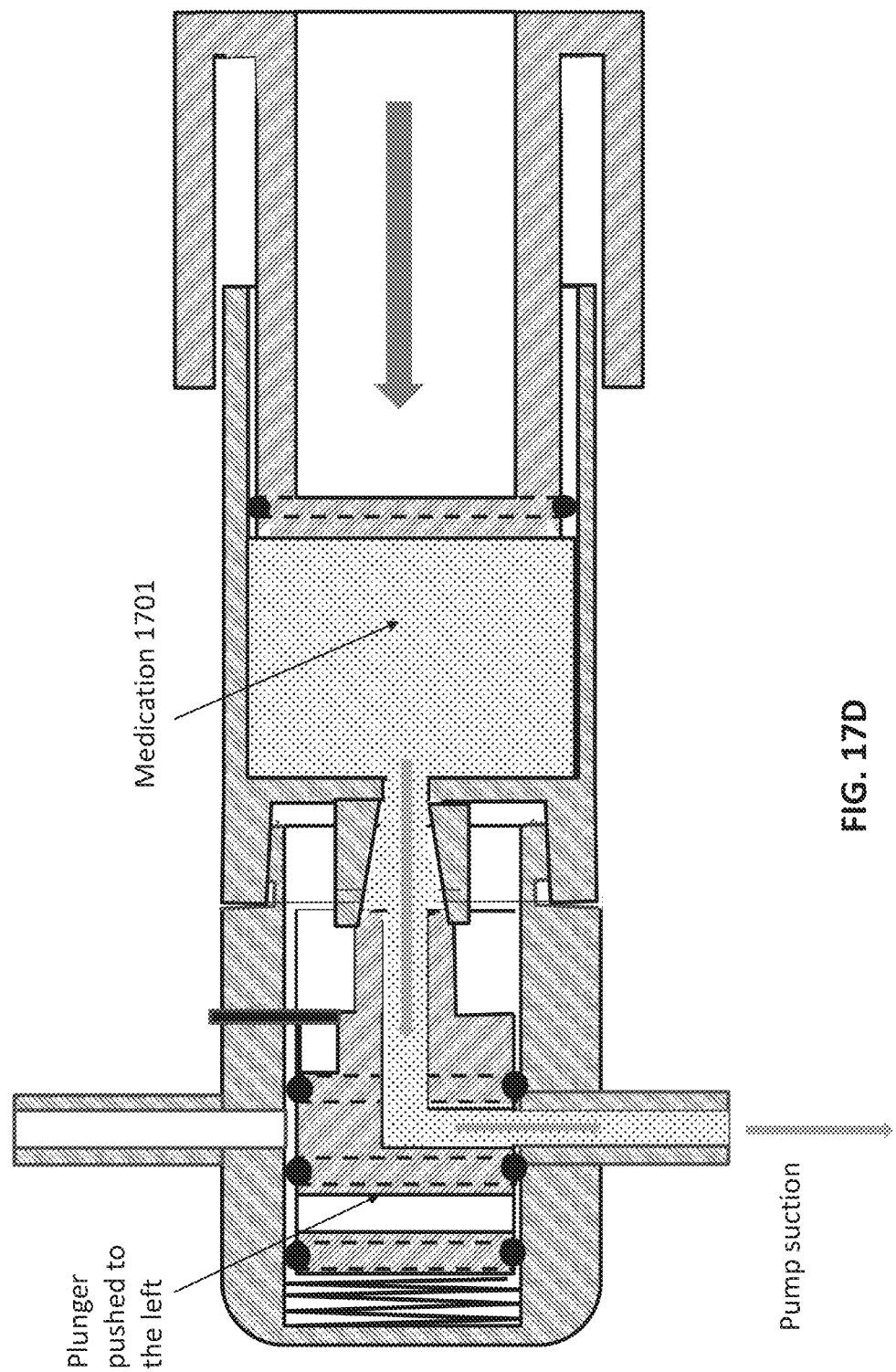

Detachable fluid container 1730 may include a container piston 1731 which allows an operator to fill detachable fluid container 1730 with fluid by pulling container piston 1731, in a similar way as filling a syringe, as shown at FIG. 17C. By attaching the two parts, the plunger moves to the left, thus blocking the fluid and opening the medication dispensing port to the pump, as shown at FIG. 17D.

An exemplary process of administering medication via a valve type dispenser is as follows:
1. Detachable fluid container 1730 is filled with the medication by the operator.
2. The system is set by the operator into medication mode, for example by pressing the interactive screen.
3. Medication flow rate is selected by the operator and operation of chamber 11 is adjusted by control unit 15.

4. Optionally, total quantity of medication is also selected by the operator.
5. Protection plug 1713 is removed by the operator.
6. Detachable fluid container 1730 is attached to housing 1710 by the operator.
7. Optionally, when total quantity is also selected, the operator confirms that detachable fluid container 1730 is attached, and only then the operation of chamber 11 is adjusted by control unit 15.
8. Optionally, when detachable fluid container 1730 is emptied a message is presented to the operator on the interactive screen.
9. When detachable fluid container 1730 is emptied it is removed by the operator.
10. Protection plug 1713 is replaced by the operator.
11. The normal flow rate is set by the operator as desired for example via the interactive screen.

Reference is now made to FIG. 18A, FIG. 18B, FIG. 18C, 18D and FIG. 18E, which are schematic illustrations of an exemplary graphic user interface (GUI) used in operating the console, according to some embodiments of the present invention. The process of command screen and control console activation of medication dispensing is shown.

Errors in medicine dispensing to patient as result of a variety of reasons should be minimized due to their tragic results. The proliferation of the internet of things (IOT) in today's designs provides an opportunity for a closed cycle authentication system as described here. By controlling the closed loop flow cycle from the physician prescription to the medicine administration to patient all errors may be minimized as desired.

Figure 19A:
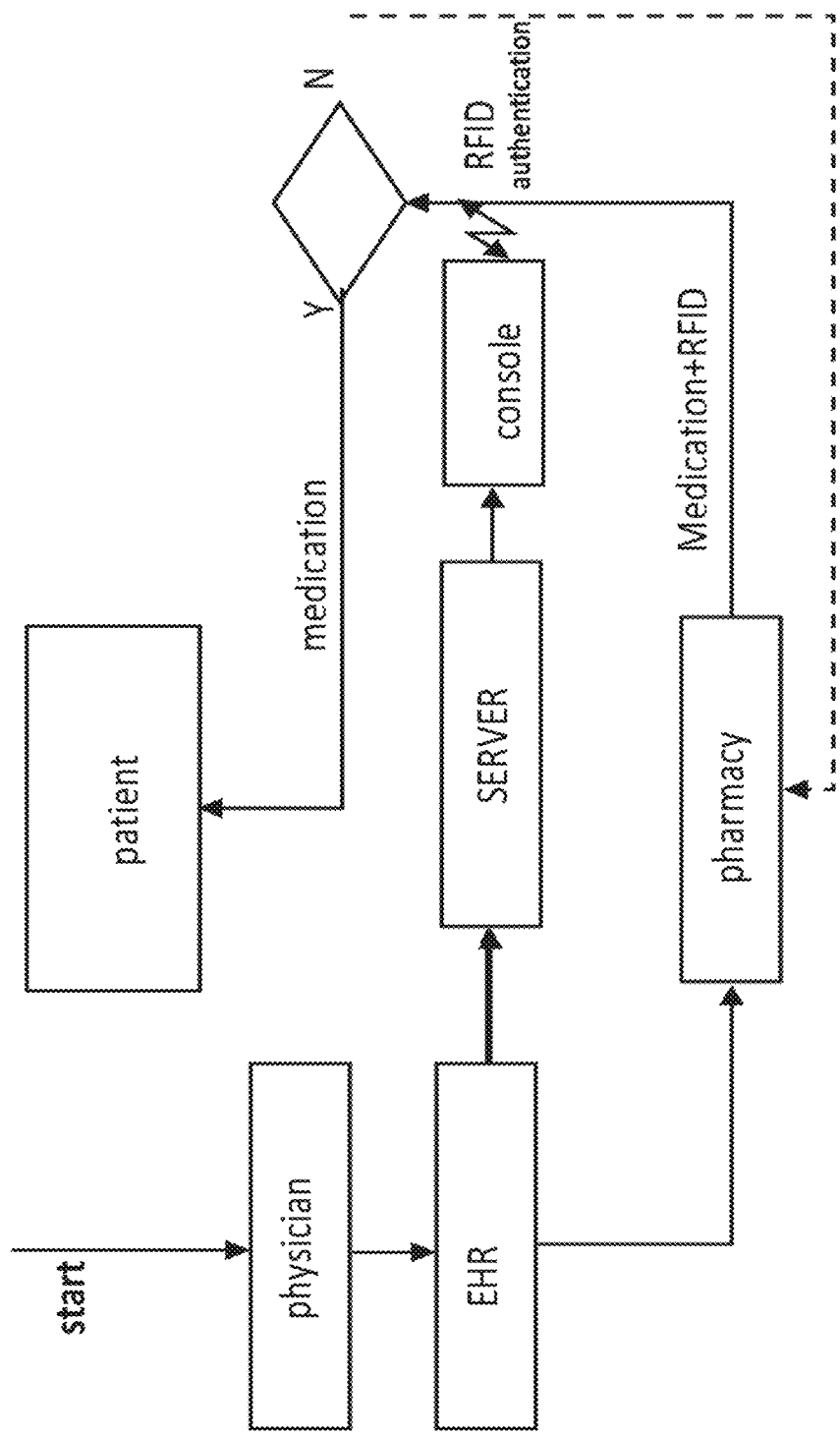
FIGS. 19A and 19B are block diagrams schematically representing a safety cycle of a medical pump use by a medical team, according to some embodiments of the present invention.
Figure 19B:
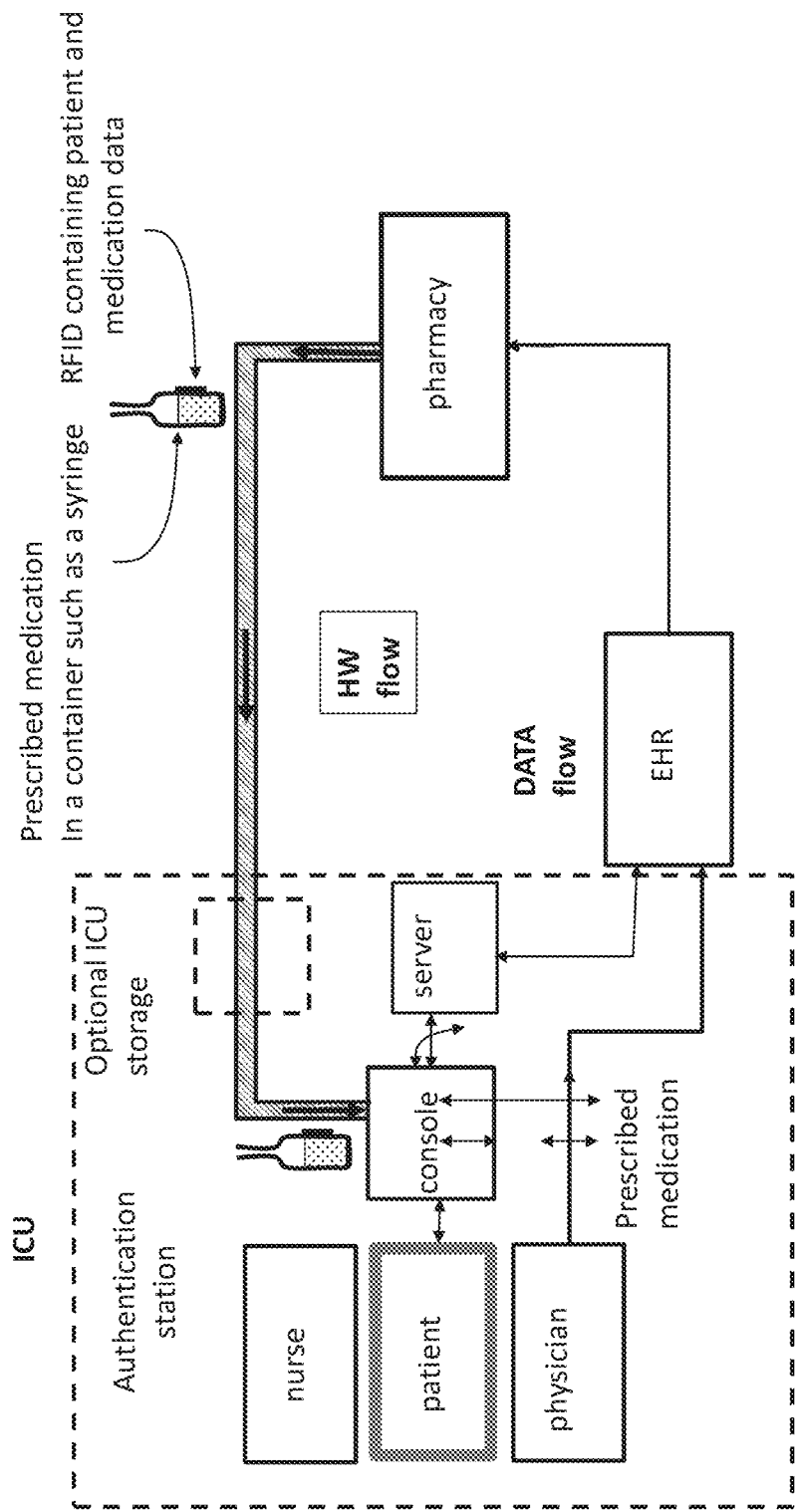

Reference is now made to FIGS. 19A and 19B, which are block diagrams schematically representing a safety cycle of a medical pump use by a medical team, according to some embodiments of the present invention.

Since radio-frequency identification devices (RFIDs) are capable of containing a large quantity of data (>8000 byte), the large capacity may be taken advantage of to add a complete medication and treatment profile to the dispensed medication which is shown later to control and authenticate the medication before administration to the patient and to check it's compliance with the physicians instructions as inserted to the electronic health record (EHR).

As shown, the closed loop is beginning with the physician's direction and terminating with the medication administration to the patient, for example by the care taking nurse.

The physician starts the cycle by punching into the EHR his recipe and direction of use for specific patient under his care.

The data is then delivered to the server and the patient console (a terminal associated with the patient, optionally stored at a bedside of the patient) as well as to the pharmacy. The data may include, for example, medication type, dose, administration and/or patient identification (ID).

Pharmacy prepares the medication in a container such, as a syringe, equipped with an RFID containing patient ID data as well as medication data and dosage. The RFID may be attached to the container of the medication, for example.

Medication container is delivered to the point of care (POC).

Medication RFID is matched with the information in the patient console.

If matching, medication is administered to patient, if mismatched the whole cycle is rechecked.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant medical pumps will be developed and the scope of the term medical pump is intended to include all such new technologies a priori.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An enteral feeding system, comprising:
   (i) a disposable system portion, comprising:
   at least two disposable inlet tubes connected to at least two fluid bags, wherein at least one bag of the at least two fluid bags contains feed material;
   a disposable fluid chamber having at least two intake openings connected to the at least two disposable inlet tubes, sealed by at least one intake valve, and an outlet opening sealed by an outlet valve;
   the disposable fluid chamber includes a piston which is sealing said fluid chamber, wherein said piston is connected to a non-disposable drive mechanism, said non-disposable drive mechanism pulls said piston to draw fluid from one of said at least two intake openings and pushes said piston to discharge said fluid into said outlet opening,
   wherein the disposable fluid chamber and said at least two disposable inlet tubes are detachable from a housing; and
   (ii) a non-disposable reusable portion, comprising:
   the non-disposable drive mechanism, the housing, and a selecting valve enclosing the at least two disposable inlet tubes, each providing fluid to one of said at least two intake openings, wherein said selecting valve closes one of said at least two disposable inlet tubes while opening another of said at least two disposable inlet tubes,
   wherein the selecting valve is not in contact with the fluid in the at least two disposable inlet tubes,
   wherein the housing includes an easy to mount mechanism for connecting and detaching therein at least part of the disposable system portion.

2. The enteral feeding system of claim 1, wherein the easy to mount mechanism of the housing comprises a first opening designed to connect to and release a plunger rod of the piston, a second opening designed to connect to and release an outlet tube connected to the outlet opening, and at least two third openings designed to connect to and release the at least two disposable inlet tubes.

3. The enteral feeding system of claim 1, wherein said at least one intake valve and said outlet valve are incorporated in an umbrella type valve box.

4. The enteral feeding system of claim 3, wherein when the piston moves up an umbrella valve flips up, an internal port of the umbrella valve is closed, fluid flows beneath the umbrella valve and suction is performed from an active inlet of the at least two intake openings.

5. The enteral feeding system of claim 3, wherein when the piston moves down an umbrella valve flips down and an internal port of the umbrella valve opens.

6. The enteral feeding system of claim 1, wherein said at least one intake valve and said outlet valve are incorporated in a valve box selected from a group consisting of: duckbill type, and poppet type.

7. The enteral feeding system of claim 1, wherein a first fluid bag of the at least two fluid bags contains the feed material and is connected to a first disposable tube of the at least two disposable inlet tubes, and a second fluid bag of the at least two fluid bags contains water and is connected to a second disposable tube of the at least two disposable inlet tubes.

8. The enteral feeding system of claim 7, wherein an amount of the feed material and an amount of the water that is pumped at a first stage is calculated so that a total amount of the feed material during a feeding cycle is equal to a prescribed amount of the feed material for the feeding cycle.

9. The enteral feeding system of claim 1, further comprising a controller configured to administer two or more of a group consisting of fluids and the feed material, from different fluid bags of the at least two fluid bags continuously according to a programmed administration plan by controlling the selecting valve that selects flow from the at least two disposable inlet tubes connected to the different fluid bags of the at least two fluid bags.

10. The enteral feeding system of claim 1, wherein said piston is connected to said non-disposable drive mechanism via a plunger rod having a slit which holds a reciprocating drive bracket of said non-disposable drive mechanism and transfers reciprocal motion of said non-disposable drive mechanism.

11. The enteral feeding system of claim 10, wherein said reciprocating drive bracket includes a fork type holder holding said slit.

12. The enteral feeding system of claim 10, wherein when the disposable fluid chamber is mounted in the housing of the non-disposable reusable portion, the reciprocating drive bracket is capable of pulling and pushing the piston thus performing a desired pumping action.

13. The enteral feeding system of claim 1, wherein at least one of: (i) wherein said non-disposable drive mechanism is controlled by an electronic control unit, or (ii) wherein said selecting valve is controlled by an electronic control unit.

14. The enteral feeding system of claim 1, wherein at least one of said selecting valve, said at least one intake valve or said outlet valve, is a one way valve.

15. The enteral feeding system of claim 1, wherein said selecting valve is instructed by an electronic control unit to alternately open and close said at least two disposable inlet tubes.

16. The enteral feeding system of claim 1, further comprising an electronic control unit which is at least one of: (i) connected to a display device, graphically displaying data related to operation of said enteral feeding system, (ii) connected to an electronic health record (EHR), (iii) provides instructions which compensate for food losses due to gastric residual volume (GRV) and reflux feeding pause, or (iv) wherein said non-disposable drive mechanism is adjusted by the electronic control unit to administer a medication from a fluid dispenser connected to one of said at least two intake openings.

17. The enteral feeding system of claim 1, wherein at least one of: (i) wherein one of said at least two disposable inlet tubes includes a fluid dispenser having a detachable fluid container, (ii) wherein said at least two intake openings are connected into an intake channel, or (iii) wherein said selecting valve is a pinch valve.

* * * * *